United States Patent
Singh Kainth et al.

(10) Patent No.: US 8,383,877 B2
(45) Date of Patent: Feb. 26, 2013

(54) ABSORBENT COMPOSITES EXHIBITING STEPPED CAPACITY BEHAVIOR

(75) Inventors: Arvinder P. Singh Kainth, Neenah, WI (US); Richard N. Dodge, II, Appleton, WI (US); David L. Zenker, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 1304 days.

(21) Appl. No.: 11/796,585

(22) Filed: Apr. 28, 2007

(65) Prior Publication Data

US 2008/0269705 A1    Oct. 30, 2008

(51) Int. Cl.
 *A61F 13/15* (2006.01)
(52) U.S. Cl. ........ 604/367; 604/378; 604/366; 604/365; 604/381; 604/302; 604/324; 604/358; 156/164; 156/566; 156/301; 156/292; 156/291; 156/298; 156/299; 156/300
(58) Field of Classification Search .................. 604/378, 604/366, 367, 385
See application file for complete search history.

(56) References Cited

U.S. PATENT DOCUMENTS

| | | |
|---|---|---|
| 3,849,241 A | 11/1974 | Butin et al. |
| 4,100,324 A | 7/1978 | Anderson et al. |
| 4,548,847 A | 10/1985 | Aberson et al. |
| 4,587,154 A | 5/1986 | Hotchkiss et al. |
| 4,604,313 A | 8/1986 | McFarland et al. |
| 4,655,757 A | 4/1987 | McFarland et al. |
| 4,724,114 A | 2/1988 | McFarland et al. |
| 4,940,464 A | 7/1990 | Van Gompel et al. |
| 5,082,723 A | 1/1992 | Gross et al. |
| 5,114,781 A | 5/1992 | Morman |
| 5,116,662 A | 5/1992 | Morman |
| 5,350,624 A | 9/1994 | Georger et al. |
| 5,393,602 A | 2/1995 | Urry |
| 5,486,166 A | 1/1996 | Bishop et al. |
| 5,490,846 A | 2/1996 | Ellis et al. |
| 5,520,672 A | 5/1996 | Urry |
| 5,629,377 A | 5/1997 | Burgert et al. |

(Continued)

FOREIGN PATENT DOCUMENTS

| | | |
|---|---|---|
| EP | 0 700 673 A1 | 3/1996 |
| GB | 2 151 272 A | 7/1985 |

(Continued)

OTHER PUBLICATIONS

American Society for Testing Materials (ASTM) Designation: D1238-70, "Standard Method for Measuring Flow Rates of Thermoplastics by Extrusion Plastometer," pp. 415-426, effective Jun. 1970.

(Continued)

*Primary Examiner* — Tatyana Zalukaeva
*Assistant Examiner* — Ilya Treyger
(74) *Attorney, Agent, or Firm* — Denise L. Stoker; Bryan R. Rosiejka

(57) ABSTRACT

An absorbent composite includes a water-insoluble fibrous matrix, a superabsorbent polymer composition that has an initial absorbent capacity of at least about 5 grams of saline per gram of superabsorbent polymer composition; and a first triggering mechanism having a first release time of between about 5 and 60 minutes, where the superabsorbent polymer composition has a second absorbent capacity that is at least about 25 % greater than the first absorbent capacity as measured by the mCRC Test.

12 Claims, 16 Drawing Sheets

U.S. PATENT DOCUMENTS

| | | | |
|---|---|---|---|
| 5,766,389 | A | 6/1998 | Brandon et al. |
| 5,820,973 | A | 10/1998 | Dodge, II et al. |
| 5,855,571 | A | 1/1999 | Steger et al. |
| 5,883,028 | A | 3/1999 | Morman et al. |
| 6,362,389 | B1 | 3/2002 | McDowall et al. |
| 6,395,830 | B1 | 5/2002 | Jonas et al. |
| 6,417,425 | B1 | 7/2002 | Whitmore et al. |
| 6,433,058 | B1 | 8/2002 | Weir et al. |
| 6,437,213 | B1 | 8/2002 | Schmidt et al. |
| 6,514,615 | B1 | 2/2003 | Sun et al. |
| 6,552,245 | B1 | 4/2003 | Roessler et al. |
| 6,579,958 | B2 | 6/2003 | Wilson |
| 6,641,134 | B1 | 11/2003 | Dobbertin et al. |
| 6,645,190 | B1 | 11/2003 | Olson et al. |
| 6,677,256 | B1 | 1/2004 | Sun et al. |
| 6,689,934 | B2 * | 2/2004 | Dodge et al. .................. 604/367 |
| 6,696,618 | B2 | 2/2004 | Dodge, II et al. |
| 6,700,034 | B1 * | 3/2004 | Lindsay et al. ............... 604/378 |
| 6,716,929 | B2 | 4/2004 | Wilson |
| 6,743,391 | B2 | 6/2004 | Sun et al. |
| 6,998,367 | B2 | 2/2006 | Qin |
| 2003/0139714 | A1 | 7/2003 | Sun et al. |
| 2004/0073181 | A1 | 4/2004 | Ramaswami Wallajapet et al. |
| 2004/0186239 | A1 | 9/2004 | Qin et al. |
| 2006/0004336 | A1 | 1/2006 | Zhang et al. |

FOREIGN PATENT DOCUMENTS

| | | |
|---|---|---|
| WO | WO 92/18079 A1 | 10/1992 |
| WO | WO 00/37009 A2 | 6/2000 |
| WO | WO 01/32117 A1 | 5/2001 |
| WO | WO 01/47569 A1 | 7/2001 |
| WO | WO 01/85081 A1 | 11/2001 |

OTHER PUBLICATIONS

Lawrence, K.D. et al., "An Improved Device for the Formation of Superfine, Thermoplastic Fibers," *NRL Report 5265*, U.S. Naval Research Laboratory, Washington, D.C., Feb. 11, 1959, pp. 1-7.

Lichstein, Bernard M., "Demand Wettability, A New Method for Measuring Absorbency Characteristics of Fabrics," *INDA Technical Symposium—Nonwoven Product Technology*, Washington, D.C., Mar. 1974, pp. 129-142.

Neumann, A.W., and R.J. Good, "Techniques of Measuring Contact Angles," Chapter 2, *Surface and Colloid Science—Experimental Methods*, vol. 11, edited by R.J. Good and R.R. Stromberg, Plenum Press, 1979, pp. 31-91.

Ring, David F. et al., "Fluid Distribution: Comparison of X-Ray Imaging Data," *Nonwovens World*, Summer 1995, pp. 67-70.

Singh, Jaspreet and Martin E. Weber, "Kinetics of One-Dimensional Gel Swelling and Collapse for Large Volume Change," *Chemical Engineering Science*, vol. 51, No. 19, 1996, pp. 4499-4508.

Wente, V.A. et al., "Manufacture of Superfine Organic Fibers," *NRL Report 4364*, U.S. Naval Research Laboratory, Washington, D.C., May 25, 1954, pp. 1-15.

Pourjavadi, A. et al., "MBA-Crosslinked Na-Alg/CMC as a Smart Full-Polysaccharide Superabsorbent Hydrogels," *Carbohydrate Polymers*, vol. 66, No. 3, Nov. 2, 2006, pp. 386-395.

* cited by examiner

ABSORBENT COMPOSITES EXHIBITING STEPPED CAPACITY BEHAVIOR

BACKGROUND

Articles, such as absorbent articles, are useful for absorbing many types of fluids, including fluids secreted or eliminated by the human body. Superabsorbent polymers (SAPs) are frequently used in absorbent articles to help improve the absorbent properties of such articles. SAPs are generally polymer based and are available in many forms, such as powders, granules, microparticles, films and fibers, for example. Upon contact with fluids, such SAPs swell by absorbing the fluids into their structures. In general, SAPs can absorb fluids insulted into such articles, and can retain such fluids to help prevent leakage and to help provide a dry feel even after fluid insult. Superabsorbent materials are often combined with water-insoluble fibers to create an absorbent composite for use in an absorbent core of an absorbent article.

There is a continuing effort to improve the performance of absorbent articles, especially at high levels of fluid saturation, to thereby reduce the occurrence of leakage and to improve fit and comfort. This is particularly significant when such articles are subjected to repeated fluid insults during use. This has become an increasing challenge as recent efforts in absorbent article design have generally focused on using higher concentrations of superabsorbent material and less fluff fiber to make the absorbent structures thinner and more flexible. However, notwithstanding the increase in total absorbent capacity obtained by increasing the concentration of superabsorbent material, such absorbent articles may still nevertheless leak during use. Such leakage may in part be the result of the absorbent core of an article having a high wet bulk in the fluid insult target zone. A high wet bulk can lead to cracking or fluid being squeezed out of the composite due to higher pressure caused by the swelling in the target zone, as well as general discomfort by the user. Therefore, there is a need for an absorbent composite which provides a reduced wet bulk in the target zone as compared to composites utilizing conventional SAPs, while generally maintaining fluid intake rate performance.

In addition, such high wet bulk may in part be the result of the absorbent composite having an insufficient fluid distribution. Poor fluid distribution decreases the full utility efficiency of absorbent composites as not all the superabsorbent material is absorbing liquid, particularly in areas located outside of the target zone. Fluid distribution in an absorbent composite is generally dependent on the amount of free liquid available for distribution, the structure and materials of the absorbent composite, and a time factor. Conventional SAPs tend to swell in the insult target zone at a moderate rate until either an entire fluid insult rate has been consumed, or until the SAP has reached its saturation point. The result is an absorbent composite that has a high wet bulk and typically does not provide desirable fluid distribution within an absorbent article. Therefore, there is a need for an absorbent composite which provides improved fluid distribution within an absorbent article as compared to composites utilizing conventional SAPs, while generally maintaining fluid intake rate performance.

SUMMARY

In response to the needs discussed above, an absorbent composition of the present invention comprises a superabsorbent polymer composition having an initial absorbent capacity of at least about 5 grams of saline (i.e., 0.9 wt % aqueous sodium chloride solution) per gram of superabsorbent polymer composition, and a first triggering mechanism, which may optionally be encapsulated, having a first release time of between about 5 and 60 minutes, where the superabsorbent polymer composition has a second absorbent capacity that is at least about 25% greater than the first absorbent capacity as measured by the Modified Centrifuge Retention Capacity (mCRC) Test. In further aspects, the absorbent composition further comprises a second triggering mechanism, which may optionally be encapsulated, having a second release time of between about 10 and 120 minutes and at least about 5 minutes longer than the first release time, where the superabsorbent polymer composition has a third absorbent capacity that at least about 25% greater than the second absorbent capacity as measured by the mCRC Test. In other aspects, the absorbent composition of further comprises a third triggering mechanism, which may optionally be encapsulated, having a third release time of between about 15 and 180 minutes and at least about 5 minutes longer than the second release time, where the superabsorbent polymer composition has a fourth absorbent capacity that is at least about 25% greater than the third absorbent capacity as measured by the mCRC Test. In still other aspects, the absorbent composition further comprises a fourth triggering mechanism, which may optionally be encapsulated, having a fourth release time of between about 20 and 240 minutes and at least about 5 minutes longer than the third release time, where the superabsorbent polymer composition has a fifth absorbent capacity that is at least about 25% greater than the fourth absorbent capacity as measured by the mCRC Test.

In some aspects, the absorbent composition has a swelling rate that is at least about 20% greater than the swelling rate of a conventional superabsorbent material as measured by the Swelling Rate Test, such as at least about 50% greater or at least about 100% greater than the swelling rate of a conventional superabsorbent material as measured by the Swelling Rate Test.

In some aspects of the present invention, an absorbent composite comprises a water-insoluble fibrous matrix, a superabsorbent polymer composition having an initial absorbent capacity of at least about 5 grams saline per gram of superabsorbent polymer composition; and a first triggering mechanism, which may optionally be encapsulated, having a first release time of between about 5 and 60 minutes, where the superabsorbent polymer composition has a second absorbent capacity that is at least about 25% greater than the first absorbent capacity as measured by the mCRC Test. In other aspects, the absorbent composite further comprises a second triggering mechanism, which may optionally be encapsulated, having a second release time of between about 10 and 120 minutes and at least about 5 minutes longer than the first release time, where the superabsorbent polymer composition has a third absorbent capacity that is at least about 25% greater than the second absorbent capacity as measured by the mCRC Test. In still other aspects, the absorbent composite further comprises a third triggering mechanism, which may optionally be encapsulated, having a third release time of between about 15 and 180 minutes and at least about 5 minutes longer than the second release time, where the superabsorbent polymer composition has a fourth absorbent capacity that is at least about 25% greater than the third absorbent capacity as measured by the mCRC Test. In yet another aspect, the absorbent composite further comprises a fourth triggering mechanism, which may optionally be encapsulated, having a fourth release time of between about 20 and 240 minutes and at least about 5 minutes longer than the third release time, where the superabsorbent polymer composition has a fifth absorbent capacity that is at least about 25% greater than the fourth absorbent capacity as measured by the mCRC Test.

In some aspects, the absorbent composite includes a superabsorbent polymer composition having a swelling rate that is at least about 20% greater than the swelling rate of a conventional superabsorbent material, such as at least about 50% greater or at least about 100% greater than the swelling rate of a conventional superabsorbent material as measured by the Swelling Rate.

In some aspects, an absorbent article comprises an absorbent core that includes a superabsorbent polymer composition having an initial absorbent capacity of at least about 5 grams saline per gram of superabsorbent polymer composition, and a first triggering mechanism, which may optionally be encapsulated, having a first release time of between about 5 and 60 minutes, where the superabsorbent polymer composition has a second absorbent capacity that is at least about 25% greater than the first absorbent capacity as measured by the mCRC Test. In other aspects, the absorbent article comprises a topsheet and a backsheet, where the absorbent core is disposed between the topsheet and the backsheet.

In some aspects, the absorbent core comprises at least about 30% by weight of the superabsorbent polymer composition. In other aspects, the absorbent core comprises about 60% to about 95% by weight of the superabsorbent polymer composition.

In some aspects, the absorbent core further comprises fluff. In other aspects, the absorbent core comprises layers. In still other aspects, at least one of the layers of the absorbent core comprises substantially only the superabsorbent polymer composition of the present invention and at least one of the layers comprises substantially only fluff. In yet other aspects, the absorbent core further comprises a surfactant.

In some aspects, the absorbent article is selected from personal care absorbent articles, health/medical absorbent articles, household/industrial absorbent articles and sports/construction absorbent articles.

Numerous other features and advantages of the present invention will appear from the following description. In the description, reference is made to exemplary embodiments of the invention. Such embodiments do not represent the full scope of the invention. Reference should therefore be made to the claims herein for interpreting the full scope of the invention. In the interest of brevity and conciseness, any ranges of values set forth in this specification contemplate all values within the range and are to be construed as support for claims reciting any sub-ranges having endpoints which are real number values within the specified range in question. By way of a hypothetical illustrative example, a disclosure in this specification of a range of from 1 to 5 shall be considered to support claims to any of the following ranges: 1-5; 1-4; 1-3; 1-2; 2-5; 2-4; 2-3; 3-5; 3-4; and 4-5.

FIGURES

The foregoing and other features, aspects and advantages of the present invention will become better understood with regard to the following description, appended claims and accompanying drawings where:

Figure 1:
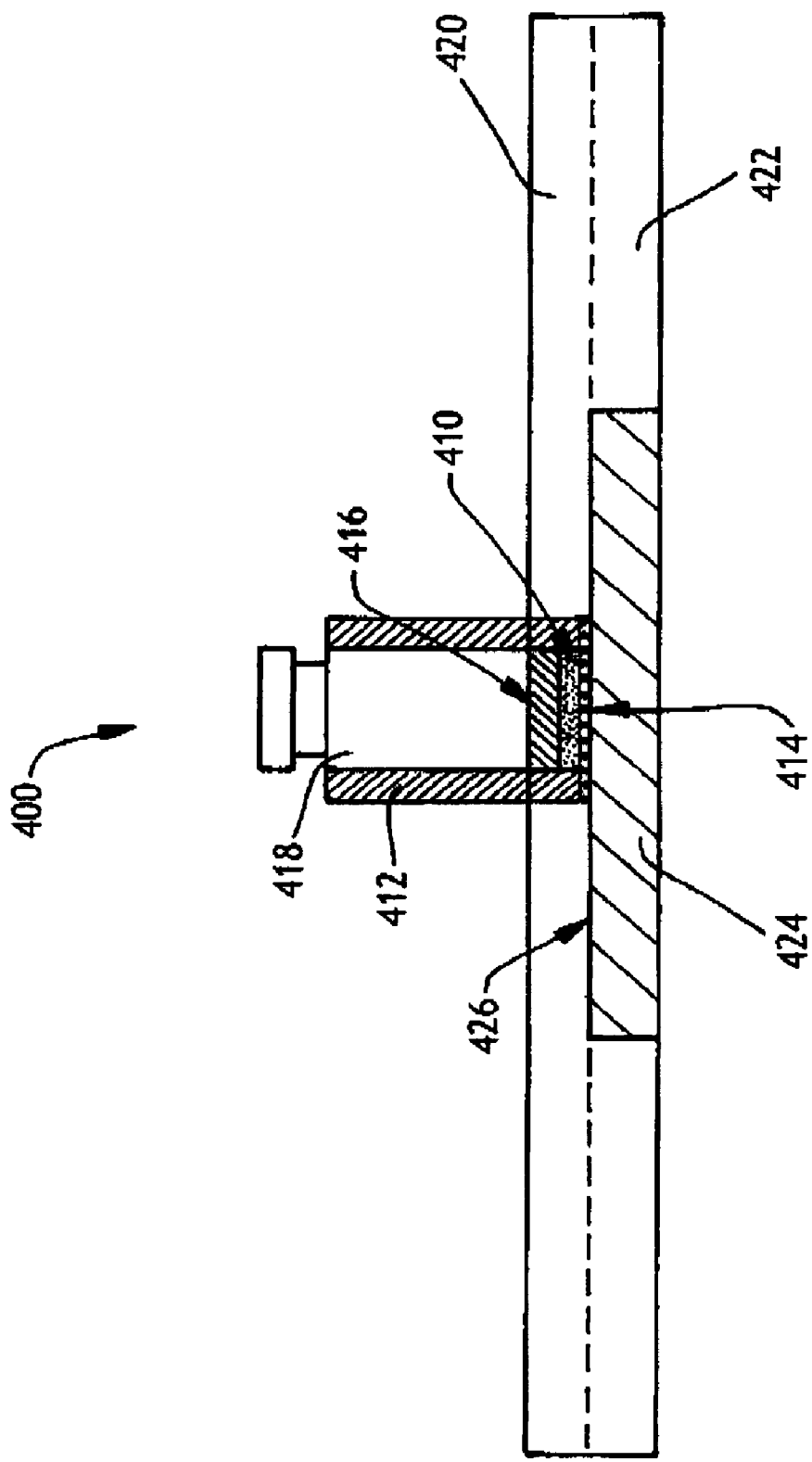
FIG. 1 is a side view of the test apparatus employed for the Absorbency Under Load Test.

Repeated use of reference characters in the present specification and drawings is intended to represent the same or analogous features or elements of the present invention.

Test Methods
Modified Centrifuge Retention Capacity (mCRC) Test

This test determines the free swelling capacity of a hydrogel-forming polymer while in a limited liquid condition. The resultant retention capacity is stated as grams of liquid retained per gram weight of the sample (g/g). In this method, 0.2000±0.0050 g of dry superabsorbent polymer composition particles of size fraction 300 to 600 μm are inserted into a teabag. The superabsorbent polymer composition particles can be pre-screened with, for example, a RO-TAP Mechanical Sieve Shaker Model B available from W. S. Tyler, Inc., having a place of business located in Mentor, Ohio, U.S.A. Sieving is conducted for 10 minutes. A heat-sealable tea bag material, such as that available from Dexter Corporation (having a place of business in Windsor Locks, Conn. U.S.A.) as model designation 1234T heat sealable filter paper works well for most applications. The bag is formed by folding a 5-inch by 3-inch (12.7-cm×7.6-cm) sample of the bag material in half and heat-sealing two of the open edges to form a 2.5-inch by 3-inch (6.4-cm×7.6-cm) rectangular pouch. The heat seals are about 0.25 inches (0.6 cm) inside the edge of the material.

After the sample is placed in the pouch, the remaining open edge of the pouch is also heat-sealed. Empty bags can also be made to serve as controls. 10 ml of saline solution (i.e., 0.9 wt % aqueous sodium chloride) is placed into a container, sufficiently large to permit the teabag to lay flat, yet small enough to prevent the saline from spreading over an excessively large area. The container for the saline should have a bottom cross-sectional area between 8 in$^2$-15 in$^2$ (52 cm$^2$-97 cm$^2$). An appropriate container is a 100 mm diameter Petri dish, catalog number 25384-056 available from VWR International (having a place of business located in West Chester, Pa., U.S.A.). The teabag is placed in the saline solution for a fixed period of time (see below), making sure that the bags are held down until they are completely wetted. Following the fixed period of immersion in saline, the teabag is centrifuged for 3 minutes at 290G-force with a variance from about 286 to about 292G-force). G-force is defined as a unit of inertial force on a body that is subjected to rapid acceleration or gravity, equal to 32 ft/sec/sec at sea level.

The absorbed quantity of saline solution is determined by measuring the weight of the teabag. The amount of solution retained by the superabsorbent polymer composition sample, taking into account the solution retained by the bag itself, is the modified Centrifuge Retention Capacity (mCRC) of the superabsorbent polymer composition at the fixed immersion time, expressed as grams of fluid per gram of superabsorbent polymer composition. More particularly, the modified centrifuge retention capacity is determined by the following equation:

$$\frac{[\text{sample and bag wt. after centrifuge}]-[\text{empty bag wt. after centrifuge}]-[\text{dry sample wt.}]}{[\text{dry sample wt.}]}$$

In order to fully characterize the free swelling capacity of the superabsorbent polymer composition under limited liquid conditions, multiple samples of superabsorbent material need to be prepared as described above and placed into multiple teabags. Each teabag must be immersed in its own 10 ml of saline solution. The time an individual sample is immersed in the saline solution should range from 5 minutes to 240, at 5 minute intervals. Each immersion time can be done with only one replicate.

Figure 17:
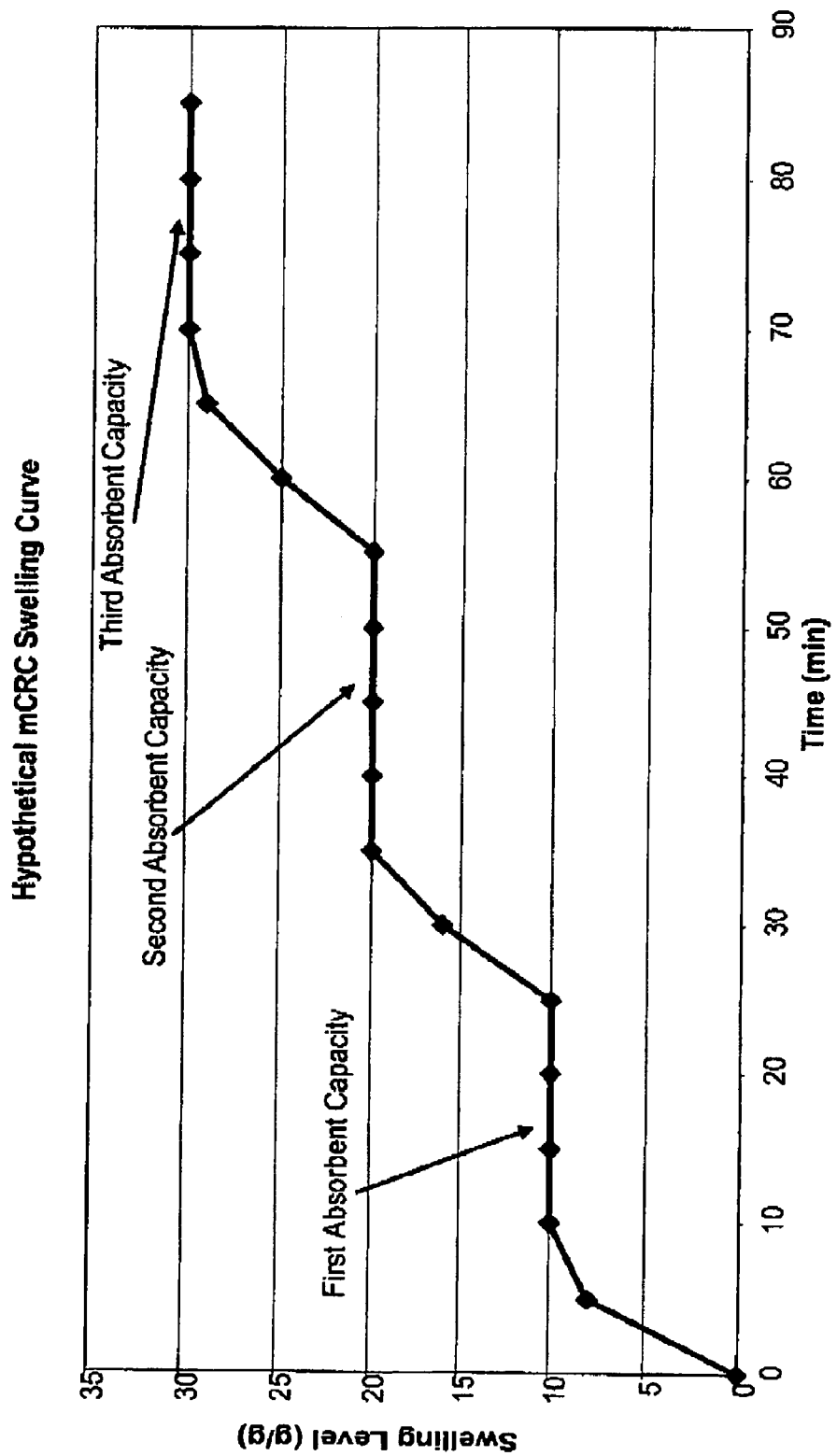
FIG. 17 is a graphical representation of stepped capacity behavior.

Typical stepped capacity swelling behavior of this invention is shown hypothetically in FIG. 17. Data points would be those capacity values measured at specific immersion times as discussed above. The first (initial) absorbent capacity can be seen as the first plateau of the swelling curve, as indicated in FIG. 17. Likewise the second absorbent capacity can be seen as the second plateau of the swelling curve, as indicated in FIG. 17. Subsequent absorbent capacities can be determined in a similar manner.

Absorbency Under Load Test (AUL)

The Absorbency Under Load (AUL) Test measures the ability of the superabsorbent polymer composition to absorb saline solution at room temperature (test solution) while the material is under a 0.9 psi load. The apparatus for testing AUL consists of:

An AUL assembly including a cylinder, a 4.4 g piston, and a 317 gram weight. The components of this assembly are described in additional detail below.

A flat-bottomed plastic tray that is sufficiently broad to allow the glass frits to lay on the bottom without contact with the tray walls. A plastic tray that is 9 inches by 9 inches (22.9 cm×22.9 cm), with a depth of 0.5 to 1inch (1.3 to 2.5 cm) is commonly used for this test method.

A 12.5 cm diameter sintered glass frit with a 'C' porosity (25-50 microns). This frit is prepared in advance through equilibration in saline. In addition to being washed with at least two portions of fresh saline, the frit must be immersed in saline for at least 12 hours prior to AUL measurements.

Whatman Grade 1, 12.5 cm diameter filter paper circles.

A supply of saline (0.9% sodium chloride in distilled water, by weight).

Referring to FIG. 1, the cylinder 412 of the AUL assembly 400 used to contain the superabsorbent polymer composition 410 is made from one-inch (2.54 cm) inside diameter clear acrylic tubing machined-out slightly to be sure of concentricity. After machining, a 400 mesh stainless steel wire cloth 414 is attached to the bottom of the cylinder 412 using an appropriate solvent that causes the screen to be securely adhered to the cylinder. Care must be taken to avoid excess solvent migrating into the open portions of the screen and reducing the open area for liquid flow. Acrylic solvent Weld-On 4 from IPS Corporation (having a place of business in Gardena, Calif., U.S.A.) is a suitable solvent. A soldering iron can be utilized to touch up the seal if unsuccessful or if it breaks. Care must be taken to maintain a flat smooth bottom and not distort the inside of the cylinder 412.

The 4.4 g piston 416 is made from 1-inch (2.5 cm) diameter solid material (e.g., PLEXIGLAS) and is machined to closely fit without binding in the cylinder 412.

A 317 gram weight 418 is used to provide a 62,053 dyne/$cm^2$ (about 0.9 psi) restraining load. The weight is a cylindrical, 1 inch (2.5 cm) diameter, stainless steel weight that is machined to closely fit without binding in the cylinder.

Unless specified otherwise, a sample 410 corresponding to a layer of at least about 300 gsm (0.16 g) of superabsorbent polymer particles is utilized for testing the AUL. The sample 410 is taken from superabsorbent polymer composition particles that are pre-screened through U.S. standard #30 mesh and retained on U.S. standard #50 mesh. The superabsorbent polymer composition particles can be pre-screened with, for example, a RO-TAP Mechanical Sieve Shaker Model B available from W. S. Tyler, Inc., Mentor, Ohio, U.S.A. Sieving is conducted for 10 minutes.

The desired amount of the sample of sieved superabsorbent polymer composition particles 410 (about 0.16 g) is weighed out on a weigh paper and evenly distributed on the wire cloth 414 at the bottom of the cylinder 412. The weight of the superabsorbent polymer composition in the bottom of the cylinder is recorded as 'SA,' for use in the AUL calculation described below. Care is taken to be sure no superabsorbent polymer composition particles cling to the wall of the cylinder. The inside of the cylinder 412 is wiped with an antistatic cloth prior to placing the superabsorbent polymer composition particles 410 into the cylinder 412. After carefully placing the 4.4 g piston 412 and 317 g weight 418 on the superabsorbent polymer composition particles 410 in the cylinder 412, the AUL assembly 400 including the cylinder, piston, weight, and superabsorbent polymer composition is weighed, and the weight is recorded as weight 'A'.

The sintered glass frit 424 (described above) is placed in the plastic tray 420, with saline 422 added to a level equal to that of the upper surface of the glass frit 424. A single circle of filter paper 426 is placed gently on the glass frit, and the AUL assembly 400 with the superabsorbent polymer particles 410 is then placed on top of the filter paper 426. The AUL assembly 400 is then allowed to remain on top of the filter paper 426 for a test period of one hour, with attention paid to keeping the saline level in the tray constant. At the end of the one hour test period, the AUL apparatus is then weighed, with this value recorded as weight 'B.'

The AUL(0.9 psi) is calculated as follows:

$$\text{AUL}(0.9\text{ psi})=(B-A)/\text{SA}$$

wherein:
A=Weight of AUL Unit with dry SAP;
B=Weight of AUL Unit with SAP after 60 minutes absorption; and
SA=Actual SAP weight.

A minimum of two tests are performed and the results are averaged to determine the AUL value under 0.9 psi load. The samples are tested at about 23° C. and about 50% relative humidity.

Fluid Intake Rate Test

Figure 2:
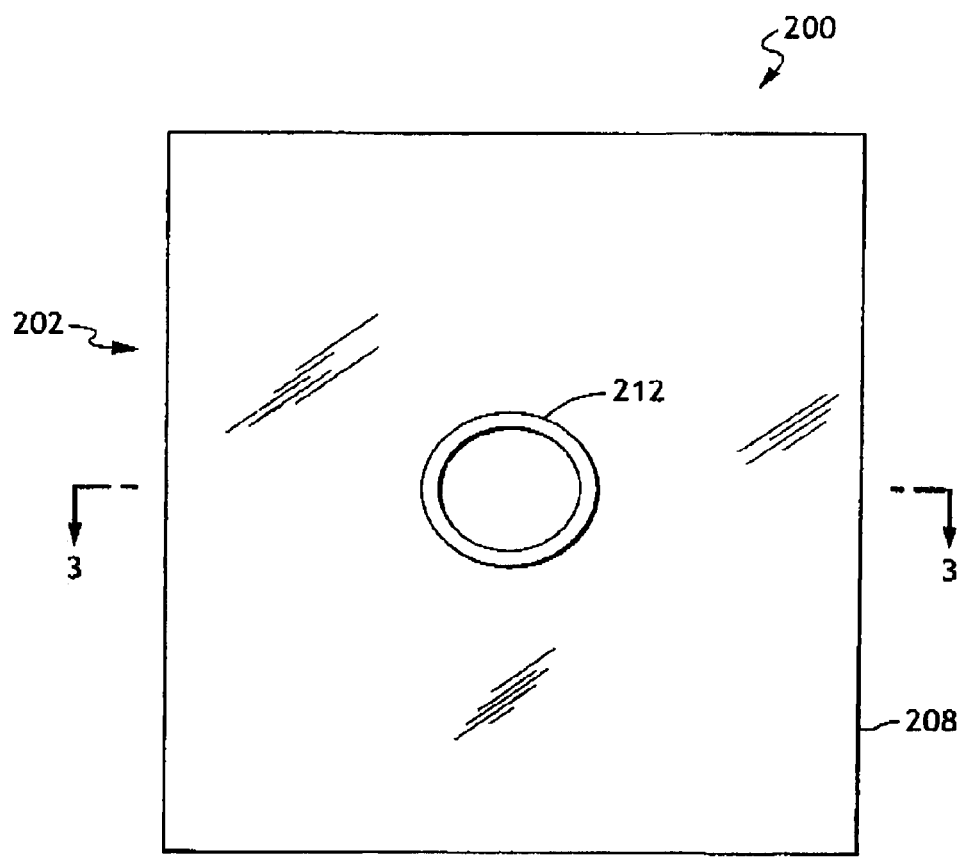
FIG. 2 is a top view of the test apparatus employed for the Fluid Intake Rate Test.
Figure 3:
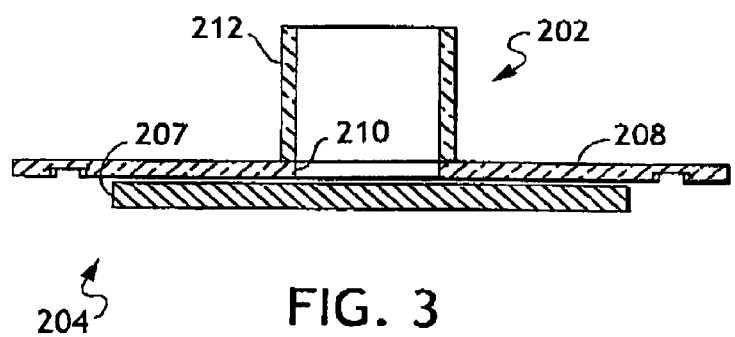
FIG. 3 is a cross-sectional side view taken along line 5-5 of the test apparatus employed for the Fluid Intake Rate Test shown in FIG. 2.

The Fluid Intake Rate (FIR) Test determines the amount of time required for an absorbent structure to take in (but not necessarily absorb) a known amount of test solution. A suitable apparatus for performing the FIR Test is shown in FIGS. 2 and 3 and is generally indicated at 200. The test apparatus 200 comprises an assembly, generally indicated at 202.

The assembly 202 comprises a generally 6 inch (15.2 cm) by 10 inch (25.4 cm) rectangular plate 208 constructed of a transparent material such as PLEXIGLAS (available from Degussa A G, a business having offices located in Dusseldorf, Germany) and having a central opening 210 formed therein. A cylinder (fluid delivery tube) 212 having an inner diameter of about one inch (2.5 cm) is secured to the plate 208 at the central opening 210 and extends upward substantially perpendicular to the plate. The central opening 210 of the plate 208 should have a diameter at least equal to the inner diameter of the cylinder 212 where the cylinder 212 is mounted on top of the plate 208. However, the diameter of the central opening 210 may instead be sized large enough to receive the outer diameter of the cylinder 212 within the opening so that the cylinder 212 is secured to the plate 208 within the central opening 210.

The weight of the assembly 202 (e.g., the plate 208 and cylinder 212) is approximately 465 grams to apply slight pressure on the absorbent sample during the FIR Test.

To run the FIR Test, an absorbent sample 207 being cut to a generally hour-glass pad shape typically used in disposable absorbent products, such as diapers, is weighed and the weight is recorded in grams. Approximate dimensions of the pad are a length of 15 inches (38 cm) with a width of 3 inches (7.6 cm) in the mid-section and a width of 4.75 inches (12 cm) at the ends. The assembly 202 is placed over the sample 207 such that the center of the cylinder 212 is generally located 4.5 inches (11.4 cm) from the front edge of the sample 207, and centered in the lateral direction. 45 grams of test solution (0.9 weight percent solution of sodium chloride in distilled water at room temperature, or an alternative based on the specific system being tested) is poured into the top of the cylinder 212 and allowed to flow down into the absorbent sample 207. A stopwatch is started when the first drop of solution contacts the sample 207 and is stopped when the liquid ring between the edge of the cylinder 212 and the sample 207 disappears. The reading on the stopwatch is recorded to two decimal places and represents the intake time (in seconds) required for the first 45 gram insult to be taken into the absorbent sample 207. Three minutes after the first 45 gram insult, an additional 25 grams of test solution is poured into the top of the cylinder 212 and allowed to flow down into the absorbent sample 207. The time required for this 25 gram insult to enter the sample is not recorded. The test solution for the 25 gram insult may be the same or different than the test solution used for the first 45 gram insult. The combination of the 45 gram insult, followed three minutes later by a 25 gram insult, together represents the first insult.

A time period of 15 minutes, from the beginning of the first 45 gram insult described above, is allowed to elapse, after which a second insult series similar to the first insult is poured into the top of the cylinder 212 and again the intake time is measured as described above. The test solution for the second insult series may be the same or different than the test solution for the first insult series. 15 minutes after the beginning of the second insult series, the procedure described above is repeated for a third insult series. An intake rate (in milliliters/second) for each of the three insults is determined by dividing the amount of solution used for the first 45 gram portion of each insult (45 grams) by the intake time measured for the corresponding insult.

At least three samples of each absorbent test are subjected to the FIR Test and the results are averaged to determine the intake rate.

Fluid Distribution Test

This test utilizes x-ray imaging to determine the amount of fluid located in various locations of the absorbent system. X-ray imaging is known in the art as discussed, for example, in an article entitled "Fluid Distribution: comparison of X-ray Imaging Data" by David F. Ring, Oscar Lijap and Joseph Pascente in Nonwovens Worldmagazine, summer 1995, at pages 65-70, which is incorporated herein by reference in a manner that is consistent herewith. Generally, this procedure compares the grey scale x-ray images of a wet and dry sample in order to calculate the liquid content at various locations. Such x-ray systems are available, for example, from Precision X-ray Inc., having a place business located at 31 Business Park Drive, Branford, Conn., U.S.A. as model no. 10561 HF 100 with enclosure. This system may use image analysis software from Optimus Inc., having a place of business located at Ft. Collins, Colo., U.S.A. as BIO-SCAN OPTI-MATE S/N OPM4101105461 version 4.11, or equivalent. The x-ray system is operated with an exposure time of 2 seconds, with a tube voltage of 50 Kv and current of 12 mA.

When a Fluid Distribution analysis is conducted in conjunction with other tests, such as the Fluid Intake Rate Test described above, the x-ray imaging should be conducted at a specific time. The sample should remain in the same gravitational orientation as used in the Fluid Intake Rate Test (i.e., horizontal). When used in conjunction with the Fluid Intake Rate Test, x-ray images are taken just prior to the next insult series. For example, x-ray images for the "first hold" (i.e., the time between or after each fluid insult) are taken just prior to the second insult series, typically within 2 minutes of the next insult series.

Additionally, a measurement of the thickness of the absorbent sample may be made before or after the x-ray image is taken. The thickness measurement may be taken at the region of the pad which aligns with the fluid delivery tube from the upper assembly described in the Fluid Intake Rate Test. Thickness measurements can be made with well known devices, such as a SONY DIGITAL INDICATOR, model U30A-F, available from Sony Precision Technology Inc., having a place of business located in Japan. Pressure applied to the sample during thickness measurement should be less than 0.1 psi.

Swelling Rate Test

This test measures the rate of swelling of a superabsorbent material with a given fluid. 0.160 grams of superabsorbent material is confined within a 5.07 $cm^2$ area Absorbency Under Load cylinder (described above in the Absorbency Under Load Test procedure) under a nominal pressure of 0.3 psi (2.1 kPa). The sample is allowed to absorb the test fluid from a dish containing excess fluid. At known time intervals, a sample is weighed after a vacuum apparatus operating at 26 inches of mercury vacuum has removed any excess interstitial fluid within the cylinder. This weight versus time data is reduced to a single diffusion coefficient value for the superabsorbent material. The diffusion coefficient is an inherent property of a specific superabsorbent material that characterizes the diffusion rate between the superabsorbent and a test fluid. A description of superabsorbent diffusion can be found in "Kinetics of One-dimensional Gel Swelling and Collapse for Large Volume Change" by J. Singh and M. E. Weber, Chemical Engineering Science Vol. 51 No.19 pp 4499-4508 (1996), which is incorporated herein by reference in a manner that is consistent herewith. The model is based upon Fick's first law of diffusion where flux is proportional to the concentration gradient.

Equipment required to carry out the Swelling Rate Test includes the following:

Electronic balance, accurate to 0.001 gram, 100-gram minimum capacity.

Figure 4:
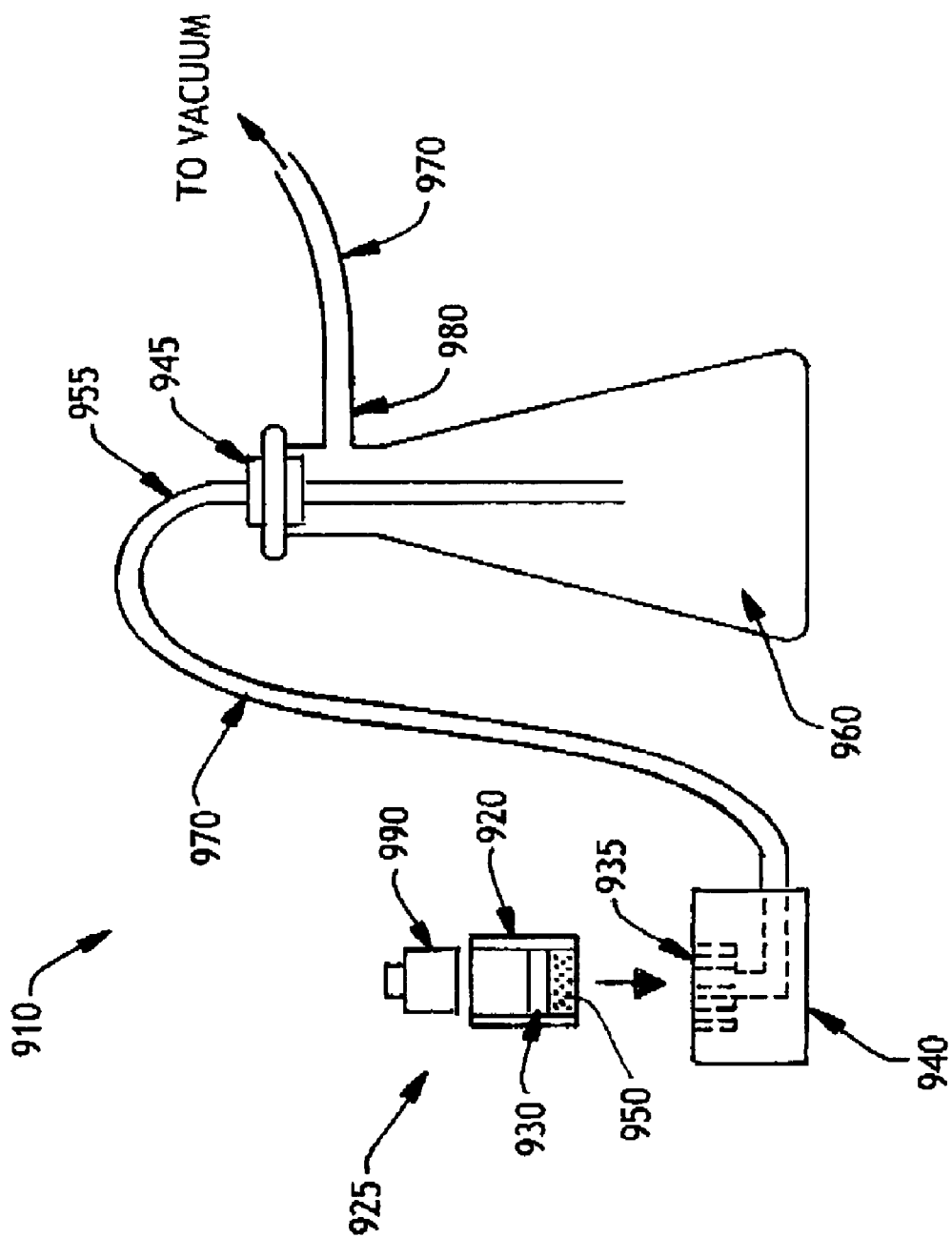
FIG. 4 is a side view of an apparatus employed for the Swell Rate Test.

With reference to FIG. 4, a Swell Rate Apparatus 910 that includes an AUL assembly 925 having a cylinder 920, a piston 930 and weight 990 as described in the Absorbency Under Load (AUL) Test method described above, except the 317 gram weight mentioned in the AUL Test is replaced with a 100 gram weight, available from VWR International (having a place of business located in West Chester, Pa., U.S.A.) as part number 12727-141, or equivalent.

The Swell Rate apparatus 910 which also includes an AUL chamber 940 used to remove interstitial liquid which is picked up during the swelling of the superabsorbent sample 950. The unit is similar to a demand absorbency tester (DAT). This test apparatus is similar to a GATS (gravimetric absorbency test system), available from M/K Systems, (having a place of business located in Danners, Mass., U.S.A.), as well as the system described by Lichstein at pages 129-142 of the INDA Technological Symposium Proceedings, March 1974, which is incorporated herein by reference in a manner that is consistent herewith. A ported disk 935 is also utilized having ports confined within a 2.5 centimeter diameter area.

Fluid bath—Petri dish, plastic weighing dish or similar which can hold an excess of fluid.

Stainless steel wire or plastic mesh screen with large open area, such as an 8 mesh plastic screen.

Vacuum source—aspirator, house vacuum line or vacuum pump.

Side arm flask 960 (FIG. 4) fitted with a rubber stopper 945 and tube 955 in the top of the flask.

Rubber or plastic tubing 970 (FIG. 4).

Timer, capable of reading 120 minutes by one-second intervals.

Paper toweling or tissue.

Anti-static cloth, for example from Ilford Photo Corp. (having a place of business located in Wyckoff, N.J., U.S.A.), part number 203547 or equivalent.

A distribution of particle sizes representative of the bulk superabsorbent material should be used for testing. This typically requires the use of a spinning riffler. An appropriate riffler is Model SR 1B available from Microscal Limited (having a place of business located in London, England). Sufficient superabsorbent material should be added to the riffler, such that each separated sample weighs 0.160±0.005 gm.

Vacuum apparatus—Using tubing 970, connect between the AUL chamber 940 and the tube in the top of the side arm flask 960. Use tubing 970 to connect between the vacuum source (not shown) and the side arm 980 of the flask 960. The purpose of the side arm flask 960 is to trap any fluid removed from the sample before it enters the vacuum system. To improve stability of the side arm flask 960, it is recommended to attach it to a ring stand or similarly secure it.

Fluid bath—Place a wire mesh (not shown) or similar large mesh plastic screen in the bottom of a fluid bath dish (not shown). Position the screen to hold the AUL assembly 925 up from the bottom of the bath and allow free access of the fluid to the sample.

To carry out the test, wipe the inside of the AUL cylinder 920 with the anti-static cloth, and weigh the cylinder 920, weight 990 and piston 930. Record the weight as CONTAINER WEIGHT in grams to the nearest milligram.

Slowly pour the 0.16±0.005 gram sample of the superabsorbent material 950 into the cylinder 920. Take care to not allow the superabsorbent material to make contact with the sides of the cylinder or it may adhere to the walls of the AUL cylinder.

Weigh the cylinder 920, weight 990, piston 930, and superabsorbent 950 and record the value on the balance, as DRY WEIGHT in grams to the nearest milligram.

Gently tap the AUL cylinder 920 until the superabsorbent material 950 is evenly distributed on the bottom of the cylinder. Gently place the piston 930 and weight 990 into the cylinder 920.

Place the test fluid (0.9 wt % aqueous sodium chloride solution) in the fluid bath with the large mesh screen on the bottom. Simultaneously start the timer and place the superabsorbent sample 950 and cylinder assembly 925 onto the screen in the fluid bath. The level in the bath should be at a height to provide at least a 1 cm positive head above the base of the cylinder. Gently swirl the sample to release any trapped air and ensure the superabsorbent material is in contact with the fluid.

Two samples at each predetermined time interval must be tested. Suggested time intervals are 30, 120, 300, 600, 1800 and 3600 seconds.

Remove the cylinder 920 from the fluid bath at the designated time and immediately place the cylinder on the vacuum apparatus (ported disk 935 on the top of the AUL chamber 940) and remove excess interstitial fluid for 10 seconds.

Wipe the exterior of the cylinder with paper toweling or tissue.

Weigh the AUL assembly (i.e., cylinder 920, piston 930 and weight 990), with the superabsorbent material and any absorbed test fluid immediately and record the weight as WET WEIGHT in grams to the nearest milligram. Record the corresponding Swelling Time in seconds as well.

The swelling level of the superabsorbent material at the designated time is calculated by the following formula:

(Wet Weight−Dry Weight)/(Dry Weight−Container Weight)=swelling level of superabsorbent material [grams liquid/grams superabsorbent]

Repeat for all time intervals needed. Exact time intervals for the weighing are dependent upon the absorption rate of the superabsorbent material. Generally, at least 6 data points of weight versus time should be taken to complete the rate curve. An initial trial may be required to determine the time intervals that span a wide enough range of swelling levels and to determine the appropriate time interval which should be used to represent the saturated capacity of the superabsorbent material. This time interval must be chosen such that the swelling level has reached a nearly equilibrium swelling level.

Using the recorded times, weights, average superabsorbent particle size and the saturated capacity of the superabsorbent the diffusion coefficient can be calculated by the following method:

At each time interval convert the swelling level of the superabsorbent material in grams liquid /gram superabsorbent material to a fractional saturation (based on the saturated capacity of the superabsorbent measured at the longest time interval). Then plot the data as fractional saturation versus time. Use the diffusion coefficient model found in the Singh and Weber reference mentioned earlier and adjust the diffusion coefficient from the model until the swelling rate curve from the model fits the experimental data using well known least square fit methods or techniques available in publicly available software such as Microsoft Excel 2003. The diffusion coefficient that best fits the experimental data can be referred to as the Swelling Rate of the superabsorbent.

It is noted that particle size determination is well known in the art. One suitable method utilizes a particle size distribution test where a sample of superabsorbent material is added to the top of a series of stacked sieves, each of which has consecutively smaller openings. The sieves are mechanically shaken for a predetermined time, then the amount of superabsorbent material on each sieve is weighed. The percent of superabsorbent material on each sieve is calculated from the initial sample weight of the superabsorbent material sample.

In the case of a superabsorbent material which exhibits the stepped capacity behavior of present invention, the swelling rate of each swelling "step" should be measured separately. The saturated capacity used for each step should be the capacity determined for the swelling step of interest.

Mannequin Test Procedure

The Mannequin Test procedure involves placing an absorbent article onto a static mannequin representing the torso of an appropriate sized human. Suitable mannequins can be obtained from Marketing Technology Services, Inc., having a place of business located in Kalamazoo, Mich., U.S.A. Fluid is added to the product by way of tubing running through the interior of the mannequin. Once liquid leaks from the product, it is detected by sensors that stop the liquid addition to that product. The amount of liquid added to the product when it leaks can be determined by weighing the products before and after they are removed from the mannequin.

Products can be evaluated for their leakage performance using the mannequin test procedure disclosed herein. Saline leakage performance is tested on a static mannequin system. The static mannequin system can be used in a forced leakage protocol in which the mannequin remains in the same position for the evaluation, in this case in the prone position (simulating the condition when the product user is laying on his/her stomach). The mannequin system uses a computer controlled set of valves and sensors to automatically deliver fluid to a particular mannequin and determine when a leakage event has occurred. The amount of liquid added and the frequency of liquid addition can be controlled. For a particular test, these conditions can be fixed. When a product has leaked, as indicated by a sensor or visually seeing the leak, it is removed and weighed to determine the amount of fluid that has been absorbed (i.e. load at leak). Optionally, after removal of the products from the mannequins, the products can be x-rayed for fluid distribution as described in the Fluid Distribution Test above. Also optionally, for each product code, data can be reported as an average load at leak, as well as a cumulative leakage distribution curve.

Definitions

It should be noted that, when employed in the present disclosure, the terms "comprises," "comprising" and other derivatives from the root term "comprise" are intended to be open-ended terms that specify the presence of any stated features, elements, integers, steps, or components, and are not intended to preclude the presence or addition of one or more other features, elements, integers, steps, components, or groups thereof.

The term "absorbent article" generally refers to devices which can absorb and contain fluids. For example, personal care absorbent articles refer to devices which are placed against or near the skin to absorb and contain the various fluids discharged from the body.

The term "coform" is intended to describe a blend of meltblown fibers and cellulose fibers that is formed by air forming a meltblown polymer material while simultaneously blowing air-suspended cellulose fibers into the stream of meltblown fibers. The coform material may also include other materials, such as superabsorbent materials. The meltblown fibers containing wood fibers and/or other materials are collected on a forming surface, such as provided by a foraminous belt. The forming surface may include a gas-pervious material, such as spunbonded fabric material, that has been placed onto the forming surface.

The term "crosslinked" used in reference to the superabsorbent polymer composition refers to any means for effectively rendering normally water-soluble materials substantially water-insoluble but swellable. Such a crosslinking means can include, for example, physical entanglement, crystalline domains, covalent bonds, ionic complexes and associations, hydrophilic associations such as hydrogen bonding, hydrophobic associations, or Van der Waals forces.

The term "disposable" is used herein to describe absorbent articles that are not intended to be laundered or otherwise restored or reused as an absorbent article after a single use.

The terms "elastic," "elastomeric," "elastically", "extensible" and "elastically extensible" are used interchangeably to refer to a material or composite that generally exhibits properties which approximate the properties of natural rubber. The elastomeric material is generally capable of being extended or otherwise deformed, and then recovering a significant portion of its shape after the extension or deforming force is removed.

The terms "fluid impermeable," "liquid impermeable," "fluid impervious" and "liquid impervious" mean that fluid such as water or bodily fluids will not pass substantially through the layer or laminate under ordinary use conditions in a direction generally perpendicular to the plane of the layer or laminate at the point of fluid contact.

The term "health/medical absorbent articles" includes a variety of professional and consumer health-care products including, but not limited to, products for applying hot or cold therapy, medical gowns (i.e., protective and/or surgical gowns), surgical drapes, caps, gloves, face masks, bandages, wound dressings, wipes, covers, containers, filters, disposable garments and bed pads, medical absorbent garments, underpads, and the like.

The term "household/industrial absorbent articles" includes construction and packaging supplies, products for cleaning and disinfecting, wipes, covers, filters, towels, disposable cutting sheets, bath tissue, facial tissue, nonwoven roll goods, home-comfort products including pillows, pads, mats, cushions, masks and body care products such as products used to cleanse or treat the skin, laboratory coats, coveralls, trash bags, stain removers, topical compositions, pet care absorbent liners, laundry soil/ink absorbers, detergent agglomerators, lipophilic fluid separators, and the like.

The terms "hydrophilic" and "wettable" are used interchangeably to refer to a material having a contact angle of water in air of less than 90 degrees. The term "hydrophobic" refers to a material having a contact angle of water in air of at least 90 degrees. For the purposes of this application, contact angle measurements are determined as set forth in Robert J. Good and Robert J. Stromberg, Ed., in "Surface and Colloid Science—Experimental Methods," Vol. II, (Plenum Press, 1979), which is incorporated herein by reference in a manner that is consistent herewith.

The term "layer" when used in the singular can have the dual meaning of a single element or a plurality of elements.

The term "MD" or "machine direction" refers to the orientation of the absorbent web that is parallel to the running direction of the forming fabric and generally within the plane formed by the forming surface. The term "CD" or "cross-machine direction" refers to the direction perpendicular to the MD and generally within the plane formed by the forming surface. Both MD and CD generally define a plane that is parallel to the forming surface. The term "ZD" or "Z-direction" refers to the orientation that is perpendicular to the plane formed by the MD and CD.

The term "meltblown fibers" refers to fibers formed by extruding a molten thermoplastic material through a plurality of fine, usually circular, die capillaries as molten threads or filaments into a high velocity, usually heated, gas (e.g., air) stream which attenuates the filaments of molten thermoplastic material to reduce their diameter. In the particular case of a coform process, the meltblown fiber stream intersects with one or more material streams that are introduced from a different direction. Thereafter, the meltblown fibers and other materials are carried by the high velocity gas stream and are deposited on a collecting surface. The distribution and orientation of the meltblown fibers within the formed web is dependent on the geometry and process conditions. Under certain process and equipment conditions, the resulting fibers can be substantially "continuous," defined as having few separations, broken fibers or tapered ends when multiple fields of view are examined through a microscope at 10×or 20×magnification. When "continuous" melt blown fibers are produced, the sides of individual fibers will generally be parallel with minimal variation in fiber diameter within an individual fiber length. In contrast, under other conditions, the fibers can be overdrawn and strands can be broken and form a series of irregular, discrete fiber lengths and numerous broken ends. Retraction of the once attenuated broken fiber will often result in large clumps of polymer.

The terms "nonwoven" and "nonwoven web" refer to materials and webs of material having a structure of individual fibers or filaments which are interlaid, but not in an identifiable manner as in a knitted fabric. The terms "fiber" and "filament" are used herein interchangeably. Nonwoven fabrics or webs have been formed from many processes such as, for example, meltblowing processes, spunbonding processes, air laying processes, and bonded-carded-web processes. The basis weight of nonwoven fabrics is usually expressed in ounces of material per square yard (osy) or grams per square meter (gsm) and the fiber diameters are usually expressed in microns. (Note that to convert from osy to gsm, multiply osy by 33.91.)

The term "particles" when used in conjunction with the term "superabsorbent" refers generally to discrete units. The units can comprise particles, granules, fibers, flakes, agglomerates, rods, spheres, needles, particles coated with fibers or other additives, pulverized materials, powders, films, and the like, as well as combinations thereof. The materials can have any desired shape such as, for example, cubic, rod-like, polyhedral, spherical or semi-spherical, rounded or semi-rounded, angular, irregular, etc.

The term "personal care absorbent article" includes, but is not limited to, absorbent articles such as diapers, diaper pants, baby wipes, training pants, absorbent underpants, child care pants, swimwear, and other disposable garments; feminine care products including sanitary napkins, wipes, menstrual pads, menstrual pants, panty liners, panty shields, interlabials, tampons, and tampon applicators; adult-care products including wipes, pads such as breast pads, containers, incontinence products, and urinary shields; clothing components; bibs; athletic and recreation products; and the like.

The term "polymer" includes, but is not limited to, homopolymers, copolymers, for example, block, graft, random, and alternating copolymers, terpolymers, etc., and blends and modifications thereof. Furthermore, unless otherwise specifically limited, the term "polymer" shall include all possible configurational isomers of the material. These configurations include, but are not limited to isotactic, syndiotactic, and atactic symmetries.

The term "polyolefin" as used herein generally includes, but is not limited to, materials such as polyethylene, polypropylene, polyisobutylene, polystyrene, ethylene vinyl acetate copolymer and the like, the homopolymers, copolymers, terpolymers, etc., thereof, and blends and modifications thereof. The term "polyolefin" shall include all possible structures thereof, which includes, but is not limited to, isotatic, synodiotactic and random symmetries. Copolymers include random and block copolymers.

Unless otherwise indicated, the term "saline" means a 0.9 wt % aqueous sodium chloride solution.

The term "sports/construction absorbent articles" includes headbands, wrist bands and other aids for absorption of perspiration, absorptive windings for grips and handles of sports equipment, and towels or absorbent wipes for cleaning and drying off equipment during use.

The terms "spunbond" and "spunbonded fiber" refer to fibers which are formed by extruding filaments of molten thermoplastic material from a plurality of fine, usually circular, capillaries of a spinneret, and then rapidly reducing the diameter of the extruded filaments.

The term "stretchable" refers to materials which may be extensible or which may be elastically extensible.

The term "superabsorbent" refers to water-swellable, water-insoluble organic or inorganic materials capable, under the most favorable conditions, of absorbing at least about 5 times their weight, or at least about 10 times their weight, or at least about 20 times their weight in an aqueous solution containing 0.9 weight percent sodium chloride.

The term "target zone" refers to an area of an absorbent core where it is particularly desirable for the majority of a fluid insult, such as urine, menses, or bowel movement, to initially contact. In particular, for an absorbent core with one or more fluid insult points in use, the insult target zone refers to the area of the absorbent core extending a distance equal to 15% of the total length of the composite from each insult point in both directions.

The term "thermoplastic" describes a material that softens when exposed to heat and which substantially returns to a non-softened condition when cooled to room temperature.

The term "% by weight" or "wt %" when used herein and referring to components of the superabsorbent polymer composition, is to be interpreted as based on the dry weight of the superabsorbent polymer composition, unless otherwise specified herein.

These terms may be defined with additional language in the remaining portions of the specification.

Detailed Description

Absorbent composites of this invention are useful in absorbent articles. An absorbent article of the present invention can have an absorbent core, and can additionally include a topsheet, a backsheet, where the absorbent core can be disposed between the topsheet and the backsheet. The absorbent core comprises an absorbent composite that includes the superabsorbent polymer composition of the present invention.

Figure 5:
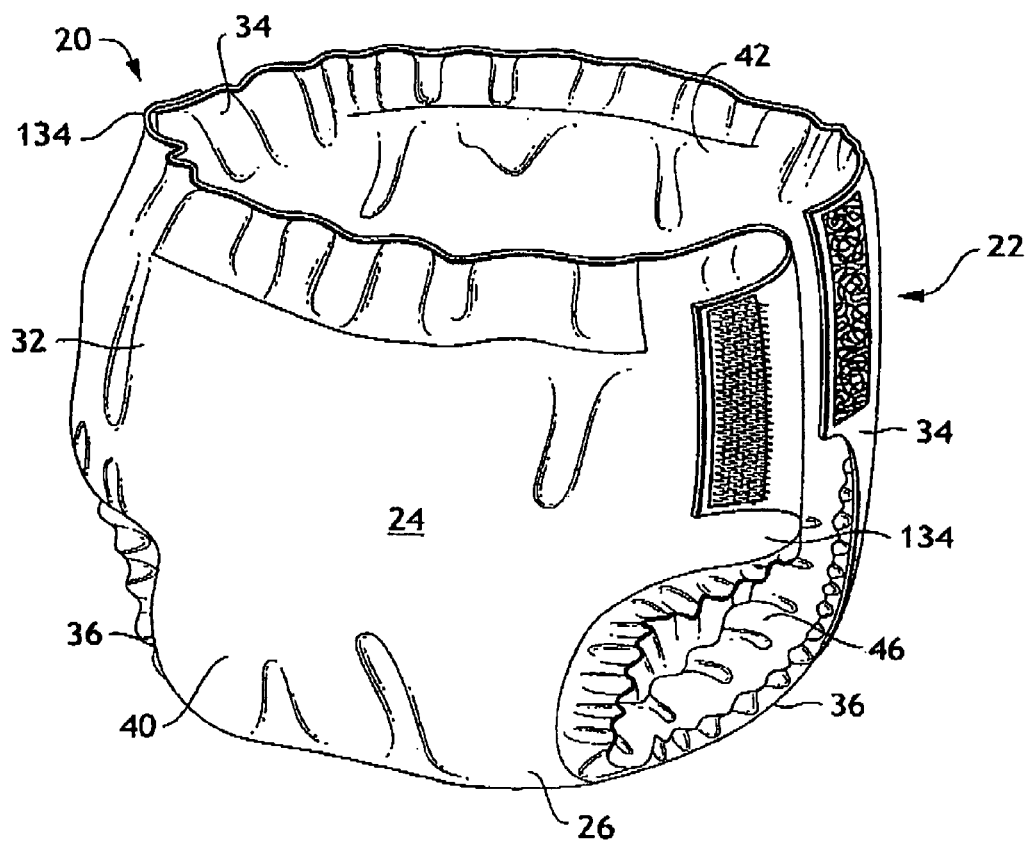
FIG. 5 is a perspective view of one embodiment of an absorbent article that may be made in accordance with the present invention.
Figure 6:
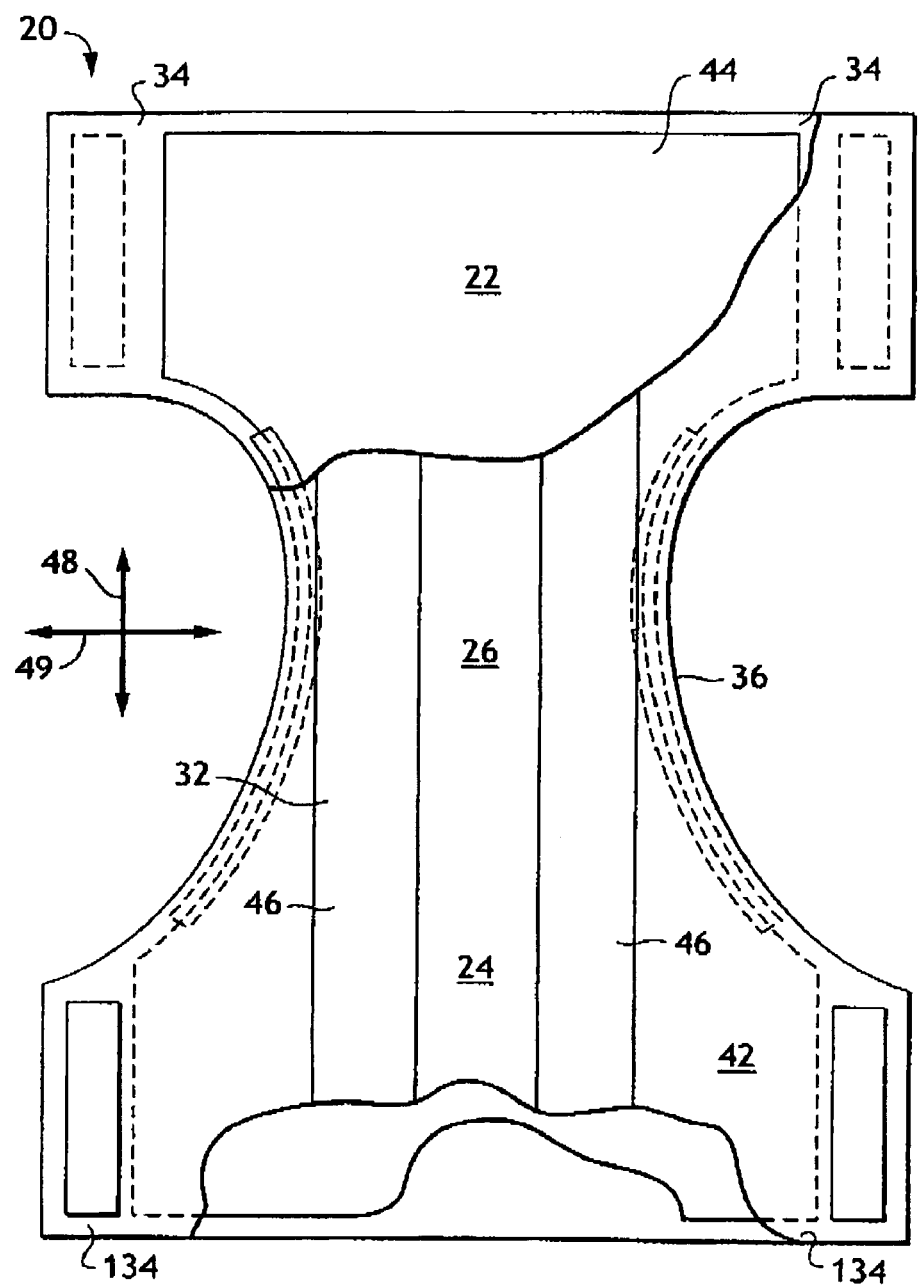
FIG. 6 is a plan view of the absorbent article shown in FIG. 5 with the article in an unfastened, unfolded and laid flat condition showing the surface of the article that faces the wearer when worn and with portions cut away to show underlying features.

To gain a better understanding of the present invention, attention is directed to FIG. 5 and FIG. 6 for exemplary purposes showing a training pant of the present invention. It is understood that the present invention is suitable for use with various other absorbent articles, including but not limited to other personal care absorbent articles, health/medical absorbent articles, household/industrial absorbent articles, sports/construction absorbent articles, and the like, without departing from the scope of the present invention.

Various materials and methods for constructing training pants are disclosed in PCT Patent Application No. WO 00/37009 published Jun. 29, 2000 by A. Fletcher et al.; U.S. Pat. No. 4,940,464 to Van Gompel et al.; U.S. Pat. No. 5,766,389 to Brandon et al., and U.S. Pat. No. 6,645,190 to Olson et al., all of which are incorporated herein by reference in a manner that is consistent herewith.

FIG. 5 illustrates a training pant in a partially fastened condition, and FIG. 6 illustrates a training pant in an opened and unfolded state. The training pant defines a longitudinal direction 48 that extends from the front of the training pant when worn to the back of the training pant. Perpendicular to the longitudinal direction 48 is a lateral direction 49.

The pair of training pants defines a front region 22, a back region 24, and a crotch region 26 extending longitudinally between and interconnecting the front and back regions. The pant also defines an inner surface adapted in use (e.g., positioned relative to the other components of the pant) to be disposed toward the wearer, and an outer surface opposite the inner surface. The training pant has a pair of laterally opposite side edges and a pair of longitudinally opposite waist edges.

The illustrated pant 20 may include a chassis 32, a pair of laterally opposite front side panels 34 extending laterally outward at the front region 22 and a pair of laterally opposite back side panels 134 extending laterally outward at the back region 24.

The chassis 32 includes a backsheet 40 and a topsheet 42 that may be joined to the backsheet 40 in a superimposed relation therewith by adhesives, ultrasonic bonds, thermal bonds or other conventional techniques. The chassis 32 further includes an absorbent core 44 for absorbing fluid body exudates exuded by the wearer such as shown in FIG. 6 disposed between the backsheet 40 and the topsheet 42. The chassis 32 may further include a pair of containment flaps 46 secured to the topsheet 42 or the absorbent core 44 for inhibiting the lateral flow of body exudates.

The backsheet 40, the topsheet 42 and the absorbent core 44 may be made from many different materials known to those skilled in the art. Any of the three layers, for instance, may be extensible and/or elastically extensible. Further, the stretch properties of each layer may vary in order to control the overall stretch properties of the product.

The backsheet 40, for instance, may be breathable and/or may be fluid impermeable. The backsheet 40 may be constructed of a single layer, multiple layers, laminates, spunbond fabrics, films, meltblown fabrics, elastic netting, microporous webs or bonded-carded-webs. The backsheet 40, for instance, can be a single layer of a fluid impermeable material, or alternatively can be a multi-layered laminate structure in which at least one of the layers is fluid impermeable.

The backsheet 40 can be biaxially extensible and optionally biaxially elastic. Elastic non-woven laminate webs that can be used as the backsheet 40 include a non-woven material joined to one or more gatherable non-woven webs or films. Stretch Bonded Laminates (SBL) and Neck Bonded Laminates (NBL) are examples of elastomeric composites.

Examples of suitable nonwoven materials are spunbond-meltblown fabrics, spunbond-meltblown-spunbond fabrics, spunbond fabrics, or laminates of such fabrics with films, or other nonwoven webs. Elastomeric materials may include cast or blown films, meltblown fabrics or spunbond fabrics composed of polyethylene, polypropylene, or polyolefin elastomers, as well as combinations thereof. The elastomeric materials may include PEBAX elastomer (available from AtoFina Chemicals, Inc., a business having offices located in Philadelphia, Pa. U.S.A.), HYTREL elastomeric polyester (available from Invista, a business having offices located in Wichita, Kans. U.S.A.), KRATON elastomer (available from Kraton Polymers, a business having offices located in Houston, Tex., U.S.A.), or strands of LYCRA elastomer (available from Invista), or the like, as well as combinations thereof. The backsheet 40 may include materials that have elastomeric properties through a mechanical process, printing process, heating process or chemical treatment. For example, such materials may be apertured, creped, neck-stretched, heat activated, embossed, and micro-strained, and may be in the form of films, webs, and laminates.

One example of a suitable material for a biaxially stretchable backsheet 40 is a breathable elastic film/nonwoven laminate, such as described in U.S. Pat. No. 5,883,028, to Morman et al., incorporated herein by reference in a manner that is consistent herewith. Examples of materials having two-way stretchability and retractability are disclosed in U.S. Pat. No. 5,116,662 to Morman and U.S. Pat. No. 5,114,781 to Morman, each of which is incorporated herein by reference in a manner that is consistent herewith. These two patents describe composite elastic materials capable of stretching in at least two directions. The materials have at least one elastic sheet and at least one necked material, or reversibly necked material, joined to the elastic sheet at least at three locations arranged in a nonlinear configuration, so that the necked, or reversibly necked, web is gathered between at least two of those locations.

The topsheet 42 is suitably compliant, soft-feeling and non-irritating to the wearer's skin. The topsheet 42 is also sufficiently liquid permeable to permit liquid body exudates to readily penetrate through its thickness to the absorbent core 44. A suitable topsheet 42 may be manufactured from a wide selection of web materials, such as porous foams, reticulated foams, apertured plastic films, woven and non-woven webs, or a combination of any such materials. For example, the topsheet 42 may include a meltblown web, a spunbonded web, or a bonded-carded-web composed of natural fibers, synthetic fibers or combinations thereof. The topsheet 42 may be composed of a substantially hydrophobic material, and the hydrophobic material may optionally be treated with a surfactant or otherwise processed to impart a desired level of wettability and hydrophilicity.

The topsheet 42 may also be extensible and/or elastomerically extensible. Suitable elastomeric materials for construction of the topsheet 42 can include elastic strands, LYCRA elastics, cast or blown elastic films, nonwoven elastic webs, meltblown or spunbond elastomeric fibrous webs, as well as combinations thereof. Examples of suitable elastomeric materials include KRATON elastomers, HYTREL elastomers, ESTANE elastomeric polyurethanes (available from Noveon, a business having offices located in Cleveland, Ohio U.S.A.), or PEBAX elastomers. The topsheet 42 can also be made from extensible materials such as those described in U.S. Pat. No. 6,552,245 to Roessler et al. which is incorporated herein by reference in a manner that is consistent herewith. The topsheet 42 can also be made from biaxially stretchable materials as described in U.S. Pat. No. 6,641,134 filed to Vukos et al. which is incorporated herein by reference in a manner that is consistent herewith.

The article 20 can optionally further include a surge management layer (not shown) which may be located adjacent the absorbent core 44 and attached to various components in the article 20 such as the absorbent core 44 or the topsheet 42 by methods known in the art, such as by using an adhesive. In general, a surge management layer helps to quickly acquire and diffuse surges or gushes of liquid that may be rapidly introduced into the absorbent structure of the article. The surge management layer can temporarily store the liquid prior to releasing it into the storage or retention portions of the absorbent core 44. Examples of suitable surge management layers are described in U.S. Pat. No. 5,486,166 to Bishop et al.; U.S. Pat. No. 5,490,846 to Ellis et al.; and U.S. Pat. No. 5,820,973 to Dodge et al., all of which are incorporated herein by reference in a manner that is consistent herewith.

The article 20 can further comprise an absorbent core 44 which comprises the absorbent composite of the present invention. The absorbent core 44 may have any of a number of shapes. For example, it may have a 2-dimensional or 3-dimensional configuration, and may be rectangular shaped, triangular shaped, oval shaped, race-track shaped, I-shaped, generally hourglass shaped, T-shaped and the like. It is often suitable for the absorbent core 44 to be narrower in the crotch portion 26 than in the rear 24 or front 22 portion(s). The absorbent core 44 can be attached in an absorbent article, such as to the backsheet 40 and/or the topsheet 42 for example, by bonding means known in the art, such as ultrasonic, pressure, adhesive, aperturing, heat, sewing thread or strand, autogenous or self-adhering, hook-and-loop, or any combination thereof.

In some aspects, the absorbent core 44 can have a significant amount of stretchability. For example, the absorbent core 44 can comprise a matrix of fibers which includes an operative amount of elastomeric polymer fibers. Other methods known in the art can include attaching superabsorbent material to a stretchable film, utilizing a nonwoven substrate having cuts or slits in its structure, and the like.

The absorbent core 44 can be formed using methods known in the art. While not being limited to the specific method of manufacture, the absorbent core can utilize a meltblown process and can optionally be formed on a coform line. Exemplary meltblown processes are described in various patents and publications, including NRL Report 4364, "Manufacture of Super-Fine Organic Fibers" by V. A. Wendt, E. L. Boone and C. D. Fluharty; NRL Report 5265, "An Improved Device For the Formation of Super-Fine Thermoplastic Fibers" by K. D. Lawrence, R. T. Lukas and J. A. Young; and U.S. Pat. No. 3,849,241 to Butin et al. and U.S. Pat. No. 5,350,624 to Georger et al., all of which are incorporated herein by reference in a manner that is consistent herewith.

To form "coform" materials, additional components are mixed with the meltblown fibers as the fibers are deposited onto a forming surface. For example, the absorbent composition of the present invention and fluff, such as wood pulp fibers, may be injected into the meltblown fiber stream so as to be entrapped and/or bonded to the meltblown fibers. Exemplary coform processes are described in U.S. Pat. No. 4,100,324 to Anderson et al.; U.S. Pat. No. 4,587,154 to Hotchkiss et al.; U.S. Pat. No. 4,604,313 to McFarland et al.; U.S. Pat. No. 4,655,757 to McFarland et al.; U.S. Pat. No. 4,724,114 to McFarland et al.; U.S. Pat. No. 4,100,324 to Anderson et al.; and U.K. Patent No. GB 2,151,272 to Minto et al., all of which are incorporated herein by reference in a manner that is consistent herewith. Absorbent, elastomeric meltblown webs containing high amounts of superabsorbent are described in U.S. Pat. No. 6,362,389 to D. J. McDowall, and absorbent, elastomeric meltblown webs containing high amounts of superabsorbent and low superabsorbent shakeout values are described in pending U.S. Publication No. 2006/0004336 to X. Zhang et al., all of which are incorporated herein by reference in a manner that is consistent herewith.

Figure 7:
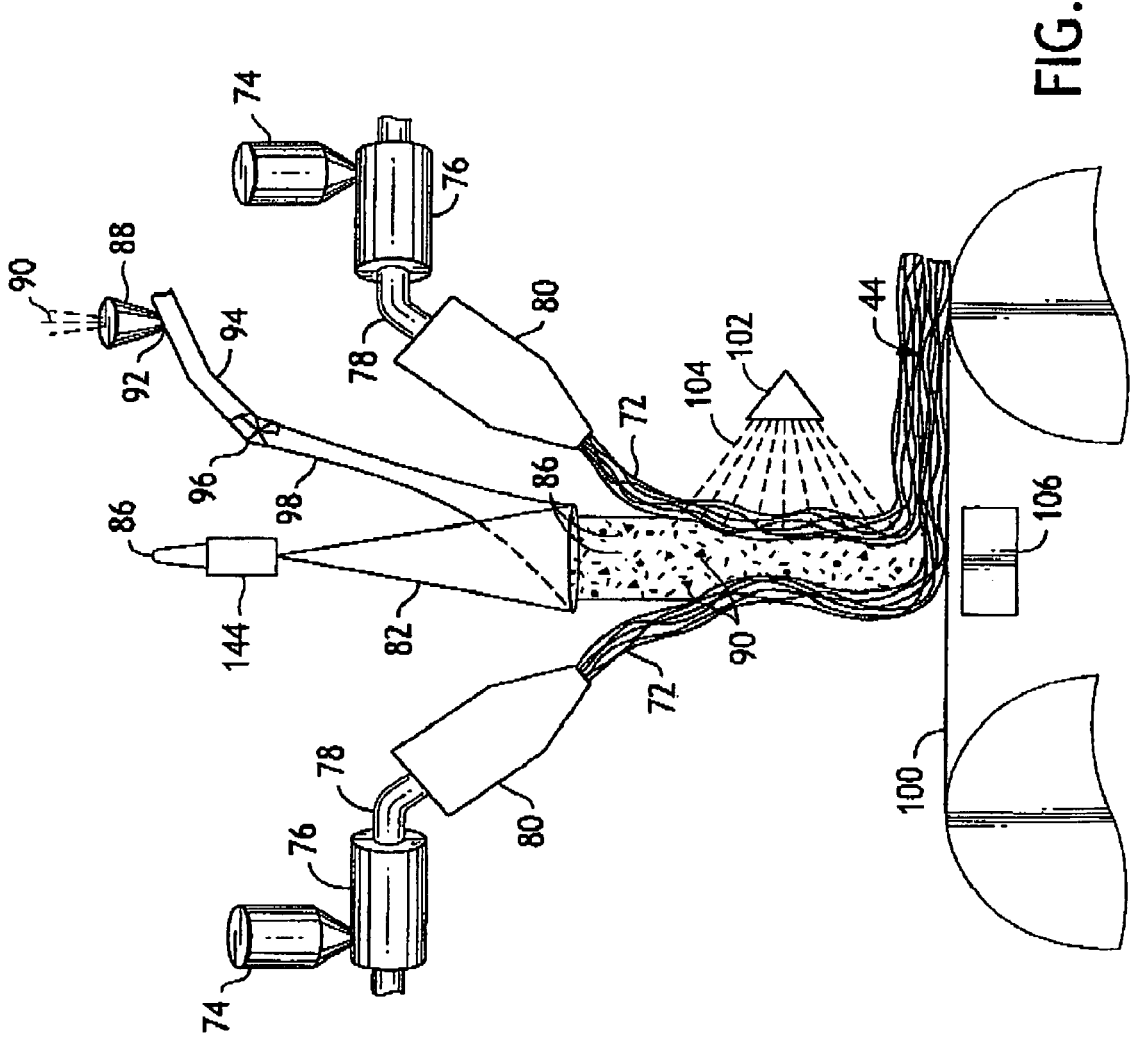
FIG. 7 is a schematic diagram of one version of a method and apparatus for producing an absorbent core.

One example of a method of forming an absorbent core 44 for use in the present invention is illustrated in FIG. 7. The dimensions of the apparatus in FIG. 7 are described herein by way of example. Other types of apparatus having different dimensions and/or different structures may also be used to form the absorbent core 44. As shown in FIG. 7, elastomeric material 72 in the form of pellets can be fed through two pellet hoppers 74 into two single screw extruders 76 that each feed a spin pump 78. The elastomeric material 72 may be a multicomponent elastomer blend available under the trade designation VISTAMAXX 2370 from ExxonMobil Chemical Company (a business having offices located in Houston, Tex., U.S.A.), as well as others mentioned herein. Each spin pump 78 feeds the elastomeric material 72 to a separate meltblown die 80. Each meltblown die 80 may have 30 holes per inch (hpi). The die angle may be adjusted anywhere between 0 and 70 degrees from horizontal, and is suitably set at about 45 degrees. The forming height may be at a maximum of about 16 inches (40.6 cm), but this restriction may differ with different equipment.

A chute 82 having a width of about 24 inches (61 cm) wide may be positioned between the meltblown dies 80. The depth, or thickness, of the chute 82 may be adjustable in a range from about 0.5 to about 1.25 inches (1.3 cm to 3.2 cm), or from about 0.75 to about 1.0 inch (1.9 cm to 2.5 cm). A picker 144 connects to the top of the chute 82. The picker 144 is used to fiberize the pulp fibers 86. The picker 144 may be limited to processing low strength or debonded (treated) pulps, in which case the picker 144 may limit the illustrated method to a very small range of pulp types. In contrast to conventional hammermills that use hammers to impact the pulp fibers repeatedly, the picker 144 uses small teeth to tear the pulp fibers 86 apart. Suitable pulp fibers 86 for use in the method illustrated in FIG. 7 include those mentioned herein, such as NB480 (available from Weyerhaeuser Co., a business having offices located in Federal Way, Wash., U.S.A.).

At an end of the chute 82 opposite the picker 144 is a superabsorbent polymer feeder 88. The feeder 88 pours the superabsorbent polymer composition 90 of the present invention into a hole 92 in a pipe 94 which then feeds into a blower fan 96. Past the blower fan 96 is a length of 4-inch (10-cm) diameter pipe 98 sufficient for developing a fully developed turbulent flow at about 5,000 feet per minute, which allows the superabsorbent polymer composition particles 90 to become distributed. The pipe 98 widens from a 4-inch (10 cm) diameter to the 24-inch by 0.75-inch (61 cm by 1.9 cm) chute 82, at which point the superabsorbent polymer composition 90 mixes with the pulp fibers 86 and the mixture falls straight down and gets mixed on either side at an approximately 45-degree angle with the elastomeric material 72. The mixture of superabsorbent polymer composition 90, pulp fibers 86, and elastomeric material 72 falls onto a wire conveyor 100 moving from about 14 to about 35 feet per minute. However, before hitting the wire conveyor 100, a spray boom 102 optionally sprays an aqueous surfactant mixture 104 in a mist through the mixture, thereby rendering the resulting absorbent core 44 wettable. The surfactant mixture 104 may be a 1:3 mixture of GLUCOPON 220 UP (available from Cognis Corporation having a place of business in Cincinnati, Ohio, U.S.A.) and AHCOVEL Base N-62 (available from Uniqema, having a place of business in New Castle, Del., U.S.A.). An under wire vacuum 106 is positioned beneath the conveyor 100 to assist in forming the absorbent core 44.

Figure 8:
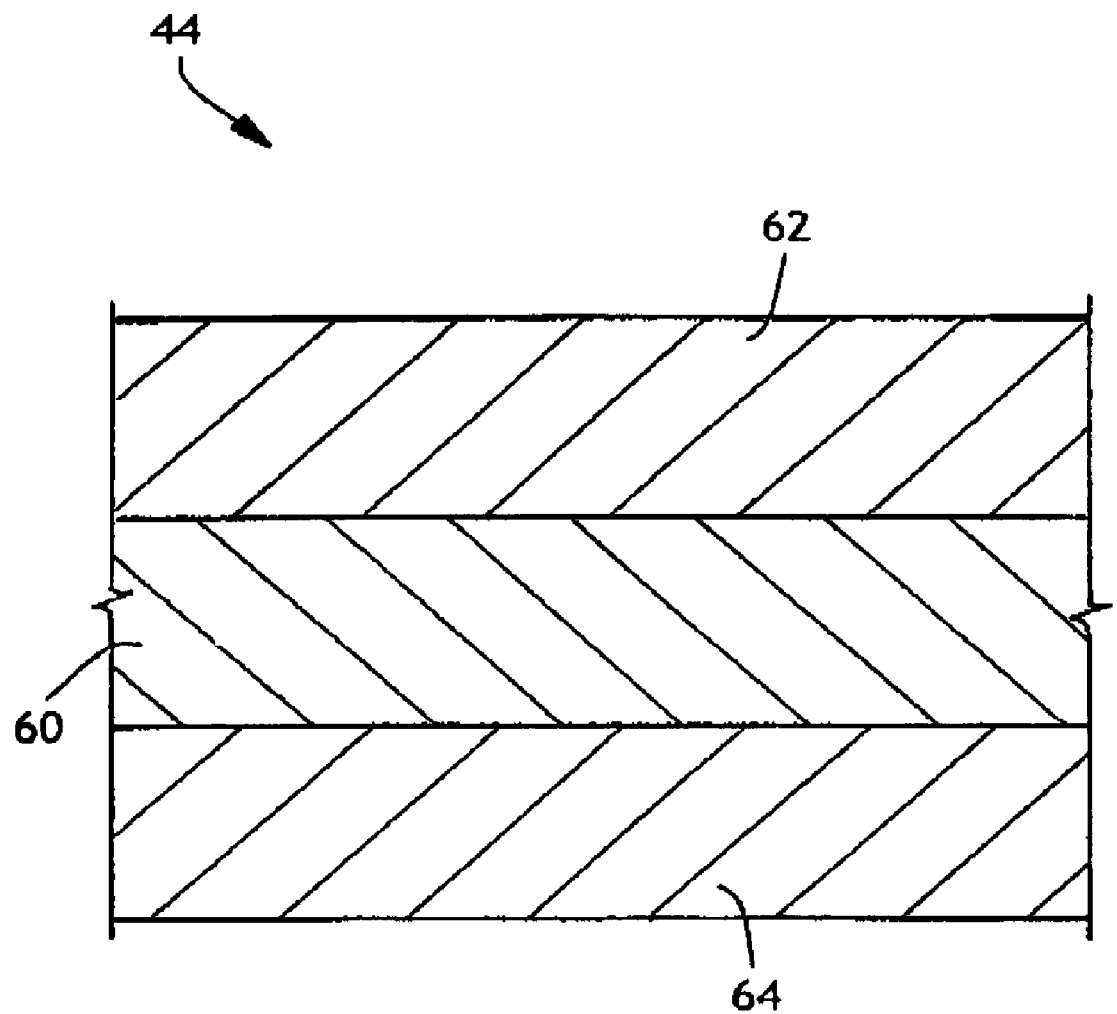
FIG. 8 is a cross-sectional side view of a layered absorbent core according to the present invention.

In general, the absorbent core 44 is often a unitary structure comprising a substantially uniform distribution of superabsorbent polymer composition particles, fibers, and any other optional additives. However, referring to FIG. 8, in some aspects, the absorbent core 44 may be further enhanced through structural modifications when combined with superabsorbent polymer composition of the present invention. For example, providing a layer 60 comprising substantially only superabsorbent polymer composition particles of the present invention sandwiched between layers 62 and 64 comprising substantially only fluff fibers, such as NB480, or other natural or synthetic fibers can result in an absorbent core having improved absorbent properties, such as fluid insult intake rate, when compared to a structure comprising a substantially uniform distribution of the superabsorbent polymer composition and fluff fibers. Such layering can occur in the z-direction of the absorbent core and may optionally cover the entire x-y area. However, the layers 60, 62 and 64 need not be discreet from one another. For example, in some aspects, the z-directional middle portion 60 of the absorbent core need only contain a higher superabsorbent polymer composition percentage (e.g., at least about 10% by weight higher) than the top layer 62 and/or bottom layer 64 of the absorbent core. Desirably, the layers are present in the area of the absorbent core that is within an insult target zone.

As referenced above, the absorbent core 44 includes absorbent material, such as the superabsorbent polymer composition of the present invention and/or fluff. Additionally, the superabsorbent polymer composition can be operatively contained within a matrix of fibers, such as polymeric fibers. Accordingly, the absorbent core 44 can comprise a quantity of the superabsorbent polymer composition and/or fluff contained within a matrix of fibers. In some aspects, the amount of superabsorbent polymer composition in the absorbent core 44 can be at least about 10% by weight of the core, such as at least about 30%, or at least about 60% by weight or at least about 90%, or between about 10% and about 99% by weight of the core, or between about 30% to about 90% by weight of the core, or between about 60% and about 95% by weight of the core to provide improved benefits. Optionally, the amount of superabsorbent polymer composition can be at least about 95% by weight of the core. In other aspects, the absorbent core 44 can comprise about 35% or less by weight fluff, such as about 20% or less, or 10% or less by weight fluff.

It should be understood that the present invention is not restricted to use with the superabsorbent polymer composition and/or fluff. In some aspects, the absorbent core 44 may additionally or alternatively include materials such as surfactants, ion exchange resin particles, moisturizers, emollients, perfumes, natural fibers, synthetic fibers, fluid modifiers, odor control additives, and combinations thereof. Alternatively, the absorbent core 44 can include a foam.

In order to function well, the absorbent core 44 can have certain desired properties to provide improved performance as well as greater comfort and confidence among the user. For instance, the absorbent core 44 can have corresponding configurations of absorbent capacities, densities, basis weights and/or sizes which are selectively constructed and arranged to provide desired combinations of absorbency properties such as liquid intake rate, absorbent capacity, liquid distribution or fit properties such as shape maintenance and aesthetics. Likewise, the components can have desired wet to dry strength ratios, mean flow pore sizes, permeabilities and elongation values.

In some aspects, absorbent core 44 can optionally include elastomeric polymer fibers. The elastomeric material of the polymer fibers may include an olefin elastomer or a non-olefin elastomer, as desired. For example, the elastomeric fibers can include olefinic copolymers, polyethylene elastomers, polypropylene elastomers, polyester elastomers, polyisoprene, cross-linked polybutadiene, diblock, triblock, tetrablock, or other multi-block thermoplastic elastomeric and/or flexible copolymers such as block copolymers including hydrogenated butadiene-isoprene-butadiene block copolymers; stereoblock polypropylenes; graft copolymers, including ethylene-propylene-diene terpolymer or ethylene-propylene-diene monomer (EPDM) rubber, ethylene-propylene random copolymers (EPM), ethylene propylene rubbers (EPR), ethylene vinyl acetate (EVA), and ethylene-methyl acrylate (EMA); and styrenic block copolymers including diblock and triblock copolymers such as styrene-isoprene-styrene (SIS), styrene-butadiene-styrene (SBS), styrene-isoprene-butadiene-styrene (SIBS), styrene-ethylene/butylene-styrene (SEBS), or styrene-ethylene/propylene-styrene (SEPS), which may be obtained from Kraton Inc. under the trade designation KRATON elastomeric resin or from Dexco, a division of ExxonMobil Chemical Company under the trade designation VECTOR (SIS and SBS polymers); blends of thermoplastic elastomers with dynamic vulcanized elastomer-thermoplastic blends; thermoplastic polyether ester elastomers; ionomeric thermoplastic elastomers; thermoplastic elastic polyurethanes, including those available from Invista Corporation under the trade name LYCRA polyurethane, and ESTANE available from Noveon, Inc., a business having offices located in Cleveland, Ohio, U.S.A.; thermoplastic elastic polyamides, including polyether block amides available from AtoFina Chemicals, Inc. (a business having offices located in Philadelphia, Pa., U.S.A.) under the trade name PEBAX; polyether block amide; thermoplastic elastic polyesters, including those available from E. I. Du Pont de Nemours Co., under the trade name HYTREL, and ARNITEL from DSM Engineering Plastics (having a place of business located in Evansville, Ind., U.S.A.) and single-site or metallocene-catalyzed polyolefins having a density of less than about 0.89 grams/cubic centimeter, available from Dow Chemical Co. (having a place of business located in Freeport, Tex., U.S.A.) under the trade name AFFINITY; and combinations thereof.

As used herein, a tri-block copolymer has an ABA structure where the A represents several repeat units of type A, and B represents several repeat units of type B. As mentioned above, several examples of styrenic block copolymers are SBS, SIS, SIBS, SEBS and SEPS. In these copolymers the A blocks are polystyrene and the B blocks are a rubbery component. Generally, these triblock copolymers have molecular weights that can vary from the low thousands to hundreds of thousands, and the styrene content can range from 5% to 75% based on the weight of the triblock copolymer. A diblock copolymer is similar to the triblock, but is of an AB structure. Suitable diblocks include styrene-isoprene diblocks, which have a molecular weight of approximately one-half of the triblock molecular weight having the same ratio of A blocks to B blocks.

In desired arrangements, the polymer fibers can include at least one material selected from the group consisting of styrenic block copolymers, elastic polyolefin polymers and copolymers and EVA/EMA type polymers.

In some particular arrangements, for example, the elastomeric material of the polymer fibers can include various commercial grades of low crystallinity, lower molecular weight metallocene polyolefins, available from ExxonMobil Chemical Company (a company having offices located in Houston, Tex., U.S.A.) under the VISTAMAXX trade designation. Some VISTAMAXX materials are believed to be metallocene propylene ethylene co-polymer. For example, in one aspect the elastomeric polymer can be VISTAMAXX PLTD 2210. In other aspects, the elastomeric polymer can be VISTAMAXX PLTD 1778. In a particular aspect, the elastomeric polymer is VISTAMAXX 2370. Another optional elastomeric polymer is KRATON blend G 2755 from Kraton Inc. The KRATON material is believed to be a blend of styrene ethylene-butylene styrene polymer, ethylene waxes and tackifying resins.

In some aspects, the elastomeric polymer fibers can be produced from a polymer material having a selected melt flow rate (MFR). In a particular aspect, the MFR can be up to a maximum of about 300. Alternatively, the MFR can be up to about 230 or 250. In another aspect, the MFR can be a minimum of not less than about 9, or not less than 20. The MFR can alternatively be not less than about 50 to provide desired performance. The described melt flow rate has the units of grams flow per 10 minutes (g/10 min). The parameter of melt flow rate is well known, and can be determined by conventional techniques, such as by employing test ASTM D 1238 70 "extrusion plastometer" Standard Condition "L" at 230° C. and 2.16 kg applied force.

As referenced above, the polymer fibers of the absorbent core 44 can include an amount of a surfactant. The surfactant can be combined with the polymer fibers of the absorbent core in any operative manner. Various techniques for combining the surfactant are conventional and well known to persons skilled in the art. For example, the surfactant may be compounded with the polymer employed to form a meltblown fiber structure. In a particular feature, the surfactant may be configured to operatively migrate or segregate to the outer surface of the fibers upon the cooling of the fibers. Alternatively, the surfactant may be applied to or otherwise combined with the polymer fibers after the fibers have been formed.

The polymer fibers can include an operative amount of surfactant, based on the total weight of the fibers and surfactant. In some aspects, the polymer fibers can include at least a minimum of about 0.1% by weight surfactant, as determined by water extraction. The amount of surfactant can alternatively be at least about 0.15% by weight, and can optionally be at least about 0.2% by weight to provide desired benefits. In other aspects, the amount of surfactant can be generally not more than a maximum of about 2% by weight, such as not more than about 1% by weight, or not more than about 0.5% by weight to provide improved performance.

If the amount of surfactant is outside the desired ranges, various disadvantages can occur. For example, an excessively low amount of surfactant may not allow fibers, such as hydrophobic meltblown fibers, to wet with the absorbed fluid. In contrast, an excessively high amount of surfactant may allow the surfactant to wash off from the fibers and undesirably interfere with the ability of the absorbent core to transport fluid, or may adversely affect the attachment strength of the absorbent core to the absorbent article. Where the surfactant is compounded or otherwise internally added to the polymer fibers, an excessively high level of surfactant can create conditions that cause poor formation of the polymer fibers and interfiber bonds.

In some configurations, the surfactant can include at least one material selected from the group that includes polyethylene glycol ester condensates and alkyl glycoside surfactants. For example, the surfactant can be a GLUCOPON surfactant, available from Cognis Corporation, which can be composed of 40% water, and 60% d-glucose, decyl, octyl ethers and oligomerics.

In other aspects of the invention, the surfactant can be in the form of a sprayed-on surfactant comprising a water/surfactant solution which includes 16 liters of hot water (about 45° C. to 50° C.) mixed with 0.20 kg of GLUCOPON 220 UP surfactant available from Cognis Corporation and 0.36 kg of AHCHOVEL Base N-62 surfactant available from Uniqema. When employing a sprayed-on surfactant, a relatively lower amount of sprayed-on surfactant may be desirable to provide the desired containment of the superabsorbent polymer particles. Excessive amounts of the fluid surfactant may hinder the desired attachment of the superabsorbent polymer particles to the molten, elastomeric meltblown fibers, for example.

An example of an internal surfactant or wetting agent that can be compounded with the elastomeric fiber polymer can include a MAPEG DO 400 PEG (polyethylene glycol) ester, available from BASF (a business having offices located in Freeport, Tex., U.S.A.). Other internal surfactants can include a polyether, a fatty acid ester, a soap or the like, as well as combinations thereof.

In some aspects, the absorbent core 44 can include fluff, such as cellulosic fibers. Such cellulosic fibers may include, but are not limited to, chemical wood pulps such as sulfite and sulfate (sometimes called Kraft) pulps, as well as mechanical pulps such as ground wood, thermomechanical pulp and chemithermomechanical pulp. More particularly, the pulp fibers may include cotton, other typical wood pulps, cellulose acetate, debonded chemical wood pulp, and combinations thereof. Pulps derived from both deciduous and coniferous trees can be used. Additionally, the cellulosic fibers may include such hydrophilic materials as natural plant fibers, milkweed floss, cotton fibers, microcrystalline cellulose, microfibrillated cellulose, or any of these materials in combination with wood pulp fibers. Suitable cellulosic fluff fibers can include, for example, NB480 (available from Weyerhaeuser Co.); NB416, a bleached southern softwood Kraft pulp (available from Weyerhaeuser Co.); COOSABSORB S, a bleached southern softwood Kraft pulp (available from Bowater Inc., a business having offices located in Greenville, S.C. U.S.A.).; SULPHATATE HJ, a chemically modified hardwood pulp (available from Rayonier Inc., a business having offices located in Jesup, Ga., U.S.A.); NF 405, a chemically treated bleached southern softwood Kraft pulp (available from Weyerhaeuser Co.); and CR 1654, a mixed bleached southern softwood and hardwood Kraft pulp (available from Bowater Inc.)

The absorbent core 44 also includes a desired amount of the superabsorbent polymer composition of the present invention. In general, superabsorbent polymers (SAPs) may be rendered water insoluble, but water swellable. These internally crosslinked polymers can be at least partially neutralized.

SAPs are manufactured by known polymerization techniques, such as by polymerization in aqueous solution by gel polymerization. The result of this polymerization process is a polymer with superabsorbent properties, which can then be reduced in size to small particles by mechanical forces and dried using drying procedures and apparatus known in the art. The drying process can be followed by pulverization of the resulting particles to the desired particle size. In general, particles too small in size swell after absorbing a fluid and can block the absorption of further fluid, while particles too large in size have a reduced surface area which can decrease the rate of absorption.

The superabsorbent polymer compositions of the present invention can be substantially homogeneously mixed with a hydrophilic composite fiber matrix or can be nonuniformly mixed. The fiber and superabsorbent particles can also be selectively placed into desired regions of the absorbent core

44, such as in the target zone for example, to better contain and absorb body exudates. The concentration of the superabsorbent particles can also vary through the thickness of the absorbent core 44. Alternatively, absorbent core 44 can include a laminate of fibrous webs and superabsorbent material or other suitable means of maintaining a superabsorbent material in a localized area.

In one aspect of the invention, the superabsorbent polymer composition is capable of swelling and absorbing fluid at an initial absorbent capacity and, when a triggering mechanism is relased, swelling and absorbing fluid at a second capacity which is at least about 25% greater than the first absorbent capacity, as measured by the Modified Centrifuge Retention Capacity (mCRC) Test described above, thus providing a stepped capacity. As used herein, "swelling" refers to the growth in mass of the superabsorbent polymer composition that occurs while fluids are being absorbed by the superabsorbent material. For swelling to occur in superabsorbent polymer compositions, fluids must be absorbed. Thus, it is understood that swelling of the superabsorbent material also means that the superabsorbent material is absorbing fluid.

The superabsorbent polymer compositions of the present invention are capable of swelling and absorbing additional fluids after a triggering mechanism is released. In one aspect, triggering mechanisms function after the superabsorbent material is saturated, or substantially saturated, with absorbed liquid. The triggering mechanism can cause the superabsorbent material to swell and absorb additional amounts of fluids as compared to the same superabsorbent material prior to release of that particular triggering mechanism.

Triggering mechanisms useful in this invention include, without limitation, materials which react to thermal, chemical, mechanical, electrical, magnetic, or radiation energy. Triggering mechanisms may also include a combination of these mechanisms or other mechanisms which can cause the superabsorbent polymer compositions to absorb additional fluids.

In some aspects of the present invention, an absorbent composite comprises a water-insoluble fibrous matrix, a superabsorbent polymer composition, and at least one triggering mechanism. In some aspects, a triggering mechanism can be incorporated directly into the superabsorbent polymer composition. In other aspects, a triggering mechanism can be located on a surface of the superabsorbent polymer composition. In yet other aspects, a triggering mechanism can be located within the absorbent composite fibrous matrix, but not necessarily in direct contact with the superabsorbent polymer composition. In still other aspects, triggering mechanisms may be incorporated into the absorbent composite through a combination of the techniques described above. It is understood that other variations of incorporating a triggering mechanism into the present invention are also suitable, and the techniques described above are provided for exemplary purposes only and should not be considered as limiting.

In addition, triggering mechanisms can be applied by means of blending, encapsulation, coating, printing, laminating, strategically blending and/or placing in a specific pocket of the composite, as well as combinations of these, or other means. A particular triggering mechanism may have time delayed effects, and only start to function when such effects are eliminated. One non-limiting example is an encapsulated triggering mechanism. The triggering materials may be used synergistically with or without any time-controlled release or delay functions.

In some aspects, the triggering mechanism can be located throughout the entire absorbent composite. In other aspects, the triggering mechanism can be located in a predetermined region of the absorbent composite. The predetermined region can be the target zone of the absorbent composite. In some aspects, around the target zone can optionally be a second superabsorbent material not affected by the triggering mechanism. The predetermined region of the absorbent composite can also be located outside of the target zone or overlapping both the target zone and an area outside the target zone.

In some aspects, an absorbent composite of the present invention comprises a first triggering mechanism. By way of example, the first triggering mechanism can have a suitable first release time of about 5 to 60 minutes. For example, in the case of an encapsulated triggering mechanism, the release time is the time required to dissolve or substantially dissolve the material which encapsulates the triggering mechanism, thereby allowing the triggering mechanism to effect the superabsorbent polymer composition. Dissolution of the triggering mechanism can be initiated through various means including, but not limited to, a fluid insult of the absorbent composite. The initial absorbent capacity of the superabsorbent material before the first triggering mechanism is released is suitably at least about 5 grams fluid per gram of superabsorbent material, such as at least about 10 grams fluid per gram of superabsorbent material, or at least about 12 grams fluid per gram of superabsorbent material, as measured by the mCRC Test. After the triggering mechanism has been released, the superabsorbent material has a second absorbent capacity that is at least about 25% greater than the initial absorbent capacity, such as at least about 30% greater or at least about 35% greater than the initial absorbent capacity.

In other aspects of the present invention, the absorbent composite can contain multiple triggering mechanisms with varying release times to release one triggering mechanism after another to provide an absorbent composite having a multiple stepped capacity (i.e., each consecutive absorbent capacity is at least about 25% higher than the previous absorbent capacity, as measured by the mCRC Test). For example, a second triggering mechanism can be used in conjunction with the first triggering mechanism, such as described above. The second triggering mechanism will desirably have a release time that is greater than the first triggering mechanism. By way of example, a suitable release time for the second triggering mechanism can be about 10 to 120 minutes from the initial fluid insult and at least 5 minutes greater than that of the first triggering mechanism release time. Release of the second encapsulated triggering mechanism will result in a third absorbent capacity that is at least about 25% greater than the second absorbent capacity obtained after release of the first triggering mechanism, such as at least about 30% greater or at least about 35% greater than the second absorbent capacity.

In further aspects of the present invention, a third triggering mechanism can be used to provide yet another stepped capacity. The third triggering mechanism will desirably have a release time that is greater than the second triggering mechanism. By way of example, a suitable third release time for the third triggering mechanism can be about 15 to 180 minutes from the initial fluid insult and at least 5 minutes greater than the second release time. Release of the third triggering mechanism will result in a fourth absorbent capacity that is at least about 25% greater than the third absorbent capacity obtained after release of the second triggering mechanism, such as at least about 30% greater or at least about 35% greater than the third absorbent capacity.

In further aspects of the present invention, a fourth triggering mechanism can be used to provide yet another stepped capacity. The fourth triggering mechanism will desirably have a release time greater than that of the third triggering mechanism. By way of example, a suitable fourth release time for the fourth triggering mechanism can be about 20 to 240 minutes and at least 5 minutes greater than the third release time. Release of the fourth encapsulated triggering mechanism will result in a fifth absorbent capacity that is at least about 25% greater than the fourth absorbent capacity obtained after release of the third triggering mechanism, such as at least about 30% greater or at least about 35% greater than the fourth absorbent capacity.

In some aspects of the present invention, superabsorbent materials, such as those having a low absorbent capacity, for example by low neutralization levels, can be triggered to swell to a higher absorbent capacity (i.e., a "step capacity" change) by a change in pH of the superabsorbent environment. For example, superabsorbent polymer compositions can be triggered to swell by the addition of a basic or an acidic compound or solution. In general, if the superabsorbent material is an anionic superabsorbent material, then the triggering mechanism will include a base. If the superabsorbent material is a cationic superabsorbent material, then the triggering mechanism will include an acid. In some aspects, a base or acid in the form of a solid may be desirable.

In some aspects, a weakly basic or weakly acidic compound may be desirable. Using weaker acids and/or bases, such as citric acid or baking soda in the absorbent composite can be safer for the user than stronger acids and/or bases such as hydrochloric acid or sodium hydroxide. In one aspect of the present invention, the desirable pH range for an absorbent composite comprising an acid triggering mechanism is a pH that is less than the original pH value of the superabsorbent material, such as about 4 to 7 when a weak acid is used, such as citric acid for example. In another aspect of the present invention, the desired pH range for an absorbent composite comprising a base triggering mechanism is a pH that is greater than the original pH value of the superabsorbent material, such as when the superabsorbent material is at 70% neutralization.

In some aspects, when an acid or base is used as the triggering mechanism, it may be desirable to blend the triggering mechanism directly into the superabsorbent material. In other aspects, it may be desirable to refrain from directly blending the acid or base into the superabsorbent material. In order to activate a triggering mechanism with a delayed effect at various lengths of time, the acid or base may be shielded from direct or immediate contact with bodily fluid. Encapsulation, for example, of the acid or base with certain chemical coatings with different thickness and dissolution kinetics can help achieve the desired time-delayed effect.

In other aspects of the present invention, the superabsorbent polymer composition can be triggered to swell by a triggering mechanism which effects a change in ionic strength after release. For example, sodium chloride in solid form can be included in the absorbent composite, which may or may not be incorporated into the superabsorbent material, and which results in a high ionic strength solution, such as 8% by weight sodium chloride, upon an initial fluid insult. The salt poisoning effect which results will limit the absorbent capacity of the superabsorbent material to a desired level. When a subsequent insult of fluid occurs which has a lower ionic strength solution, such as aqueous 0.9% sodium chloride, the absorbent capacity will increase to a new, higher limit. This stepped capacity increase can continue until the ionic strength of the superabsorbent environment is equal to, or less than, the ionic strength of the insulting fluid.

Figure 9:
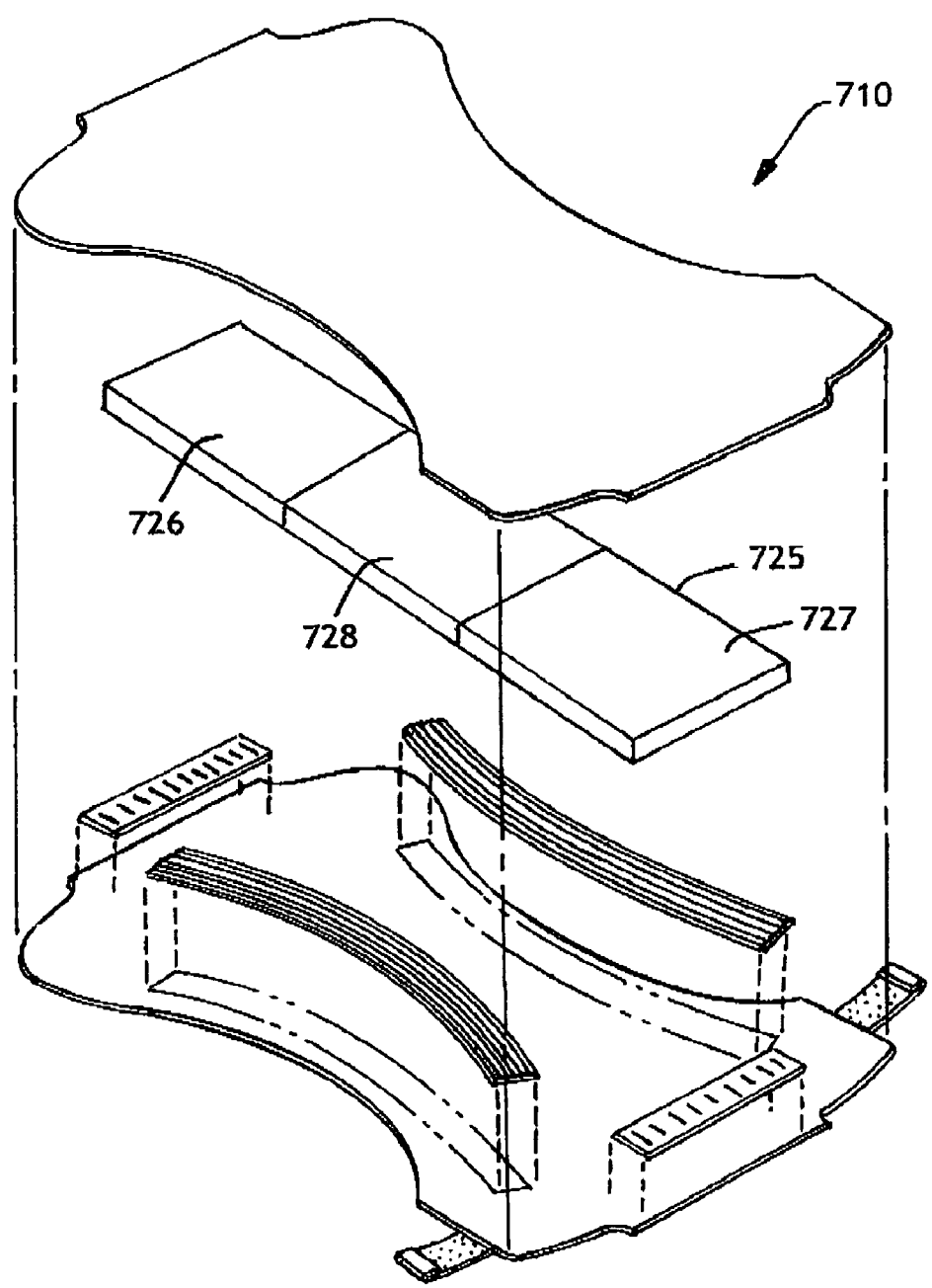
FIG. 9 is a perspective view of an absorbent article according to one aspect of the present invention.

In some aspects, superabsorbent materials capable of stepped capacity swelling according to the present invention can be distributed throughout the absorbent composite. In other aspects, the superabsorbent polymer compositions can be localized to predetermined areas of an absorbent composite. For example, FIG. 9 shows an absorbent article 710 having an absorbent core 725 comprising an absorbent composite according to one aspect of the present invention. Absorbent core 725 can include the superabsorbent polymer composition of the present invention located in a target zone region 728. An optional second superabsorbent material can be placed outside the target zone region 728 in outside regions 726, 727. The superabsorbent polymer composition of the present invention that is located in the target zone region 728 has the ability to swell relatively quickly (compared to a conventional SAP) once a triggering mechanism is released, but will have a limited absorbent capacity. Fluid from each fluid insult that cannot be absorbed by the superabsorbent material of the present invention located in the target zone region 728 will be distributed and absorbed by the superabsorbent polymer composition in the outside regions 726, 727. The absorbent capacity of the superabsorbent polymer composition in the target zone region 728 can then be increased by release of another triggering mechanism such that additional fluid insulted into the target zone will quickly swell the superabsorbent material to a higher absorbent capacity limit, and the excess fluid will once again distribute into the outside regions 726, 727. Each limited absorbent capacity of the stepped capacity superabsorbent polymer composition results in lower overall swelling thickness in the target zone when compared to composites utilizing conventional SAPs, because excess fluid in the present invention is distributed away from the target zone region 728. The result is an absorbent composite that provides greater comfort and confidence to the user.

Superabsorbent materials useful in this invention can initially absorb (i.e., prior to release of a first triggering mechanism) at least about 5 grams of saline (i.e., 0.9 wt % aqueous sodium chloride solution) per gram of superabsorbent, such as at least about 10 grams of saline per gram of superabsorbent, or 12 grams of saline per gram of superabsorbent, as measured by the mCRC Test. Stepped capacity superabsorbent materials useful in this invention can result in an absorbent capacity that is at least about 25% greater after release of a triggering mechanism as compared to the same superabsorbent material prior to release of the triggering mechanism. In some aspects, the superabsorbent polymer compositions of the present invention have a swelling rate that is at least about 20% greater than the swelling rate of conventional SAPs, such as at least about 50% greater, or 75% greater, or 100% greater than the swelling rate of conventional SAPs, as measured by the Swelling Rate Test.

The superabsorbent polymer compositions according to the invention can be employed in many products including sanitary towels, diapers, or wound coverings, and they have the property that they rapidly absorb large amounts of menstrual blood, urine, or other body fluids, for example. Since the superabsorbent materials according to the invention retain the absorbed liquids even under pressure and are also capable of distributing further liquid within the construction in the swollen state, they are more desirably employed in higher concentrations, with respect to other absorbent core components, such as fluff, when compared to conventional current superabsorbent compositions. They are also suitable for use as a homogeneous superabsorber layer without fluff content within an absorbent article construction, as a result of which particularly thin articles are possible.

The preparation of laminates in the broadest sense, and of extruded and coextruded, wet- and dry-bonded, as well as subsequently bonded structures, are possible as further preparation processes. A combination of these possible processes with one another is also possible.

In addition to the articles described above, the superabsorbent polymer compositions according to the invention may also be employed in absorbent articles that are suitable for further uses. In particular, the superabsorbent polymer compositions of this invention can be used in personal care absorbent articles, health/medical absorbent articles, household/industrial absorbent articles, sports/construction absorbent articles, and the like.

Figure 10A:
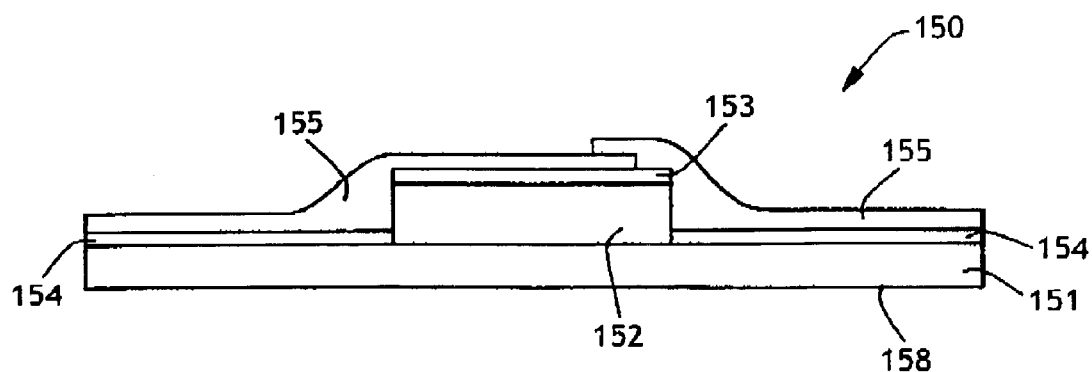
FIG. 10A is a cross-section side view of an absorbent bandage of the present invention.
Figure 10B:
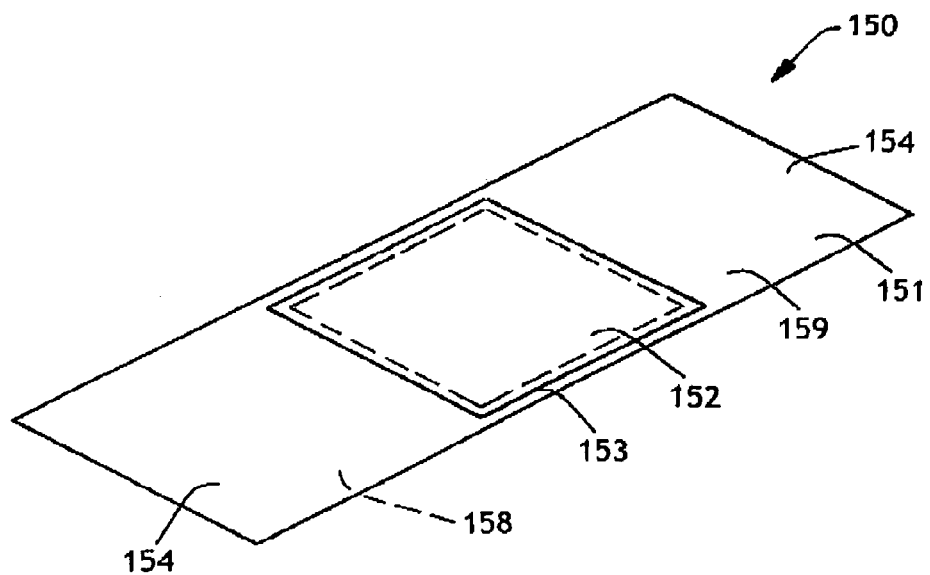
FIG. 10B is a top perspective view of an absorbent bandage of the present invention.

In addition to the absorbent article described above, the present invention may be exemplified as an absorbent bandage. Attention is directed to FIGS. 10A and 10B, which show a possible configuration for a bandage of the present invention. FIG. 10A shows a cross-section view of the absorbent bandage with optional layers described below. FIG. 10B shows a perspective view of the bandage of the present invention with some of the optional or removable layers not being shown. The absorbent bandage 150 has a strip 151 of material having a body-facing side 159 and a second side 158 which is opposite the body-facing side. The strip is essentially a backsheet and is desirably prepared from the same materials described above for the backsheet. In addition, the strip may be an apertured material, such as an apertured film, or material which is otherwise gas permeable, such as a gas permeable film. The strip 151 supports an absorbent core 152 comprising the superabsorbent polymer composition of the present invention which is attached to the body-facing side 159 of the strip. In addition, an absorbent protective layer 153 may be applied to the absorbent core 152 and can be coextensive with the strip 151.

The absorbent bandage 150 of the present invention may also have a pressure sensitive adhesive 154 applied to the body-facing side 159 of the strip 151. Any pressure sensitive adhesive may be used, provided that the pressure sensitive adhesive does not irritate the skin of the user. Suitably, the pressure sensitive adhesive is a conventional pressure sensitive adhesive which is currently used on similar conventional bandages. This pressure sensitive adhesive is desirably not placed on the absorbent core 152 or on the absorbent protective layer 153 in the area of the absorbent core 152. If the absorbent protective layer is coextensive with the strip 151, then the adhesive may be applied to areas of the absorbent protective layer 153 where the absorbent core 152 is not located. By having the pressure sensitive adhesive on the strip 151, the bandage is allowed to be secured to the skin of a user in need of the bandage. To protect the pressure sensitive adhesive and the absorbent, a release strip 155 can be placed on the body-facing side 159 of the bandage. The release liner may be removably secured to the article attachment adhesive and serves to prevent premature contamination of the adhesive before the absorbent article is secured to, for example, the skin. The release liner may be placed on the body-facing side of the bandage in a single piece (not shown) or in multiple pieces, as is shown in FIG. 10A.

In another aspect of the present invention, the absorbent core of the bandage may be placed between a folded strip. If this method is used to form the bandage, the strip is suitably fluid permeable.

Figure 11:
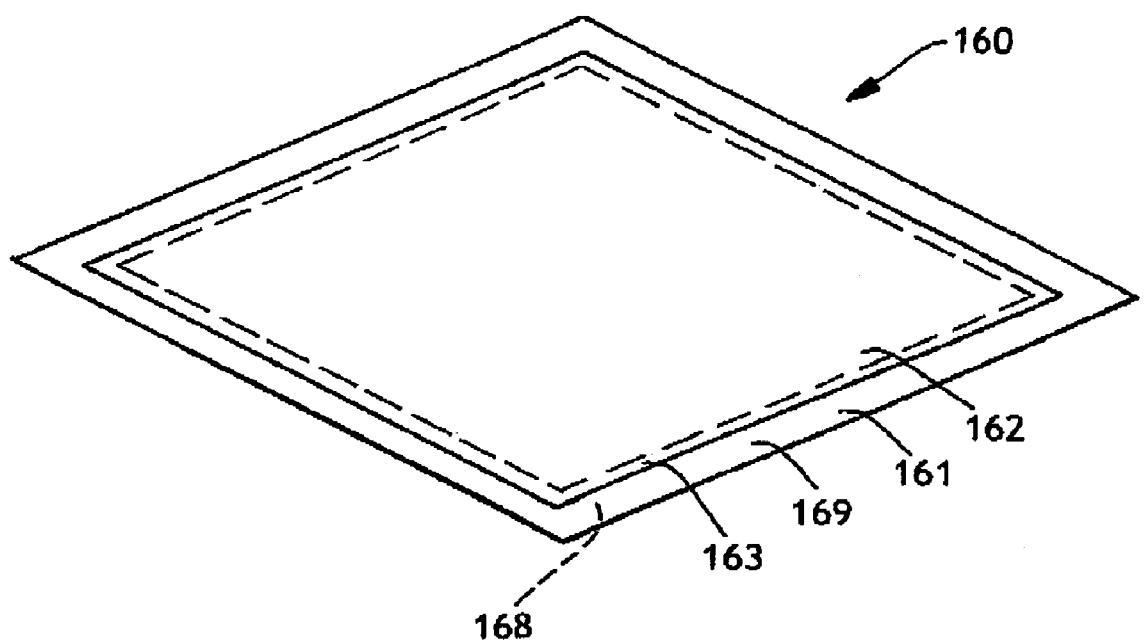
FIG. 11 is a top perspective view of an absorbent bed or furniture liner of the present invention.

Absorbent furniture and/or bed pads or liners are also included within the present invention. As is shown in FIG. 11, a furniture or bed pad or liner 160 (hereinafter referred to as a "pad") is shown in perspective. The pad 160 has a fluid impermeable backsheet 161 having a furniture-facing side or surface 168 and an upward facing side or surface 169 which is opposite the furniture-facing side or surface 168. The fluid impermeable backsheet 161 supports the absorbent core 162 which comprises the superabsorbent polymer composition of the present invention, and which is attached to the upward facing side 169 of the fluid impermeable backsheet. In addition, an optional absorbent protective layer 163 may be applied to the absorbent core. The optional substrate layer of the absorbent core can be the fluid impermeable layer 161 or the absorbent protective layer 163 of the pad.

To hold the pad in place, the furniture-facing side 168 of the pad may contain a pressure sensitive adhesive, a high friction coating or other suitable material which will aid in keeping the pad in place during use. The pad of the present invention can be used in a wide variety of applications including placement on chairs, sofas, beds, car seats and the like to absorb any fluid which may come into contact with the pad.

Figure 12:
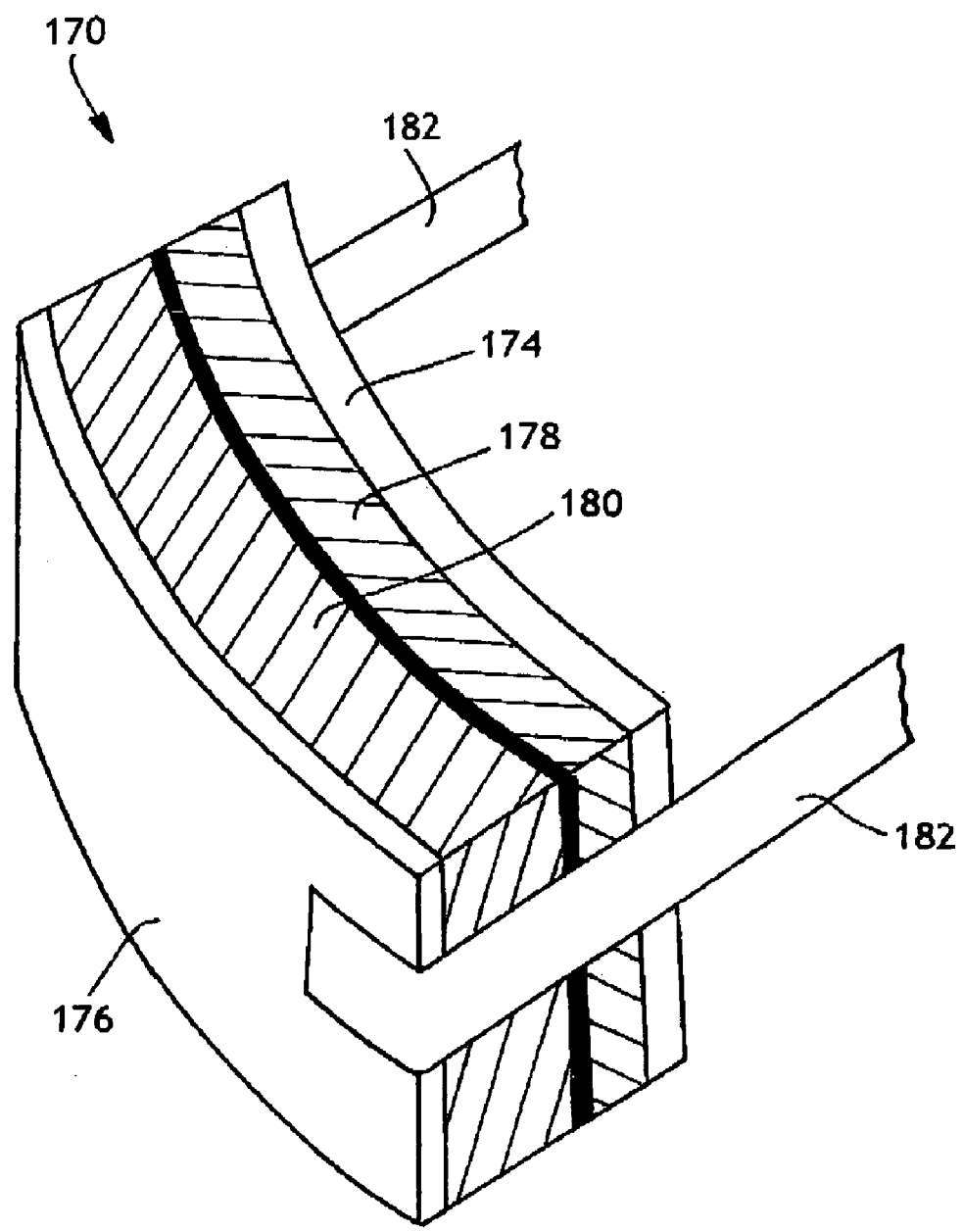
FIG. 12 is a perspective view of an absorbent sweatband of the present invention.

Sports or construction accessories, such as an absorbent headband for absorbing perspiration or drying off equipment are also included within the present invention. As is shown in FIG. 12, an absorbent sweatband 170 is shown in perspective. The sweatband 170 has an absorbent core 180 disposed between an optional topsheet 174 and/or an optional fluid impervious backsheet 176. The absorbent core 180 comprises the superabsorbent polymer composition of the present invention, and in some aspects can include an optional additional region 178 (such as a distribution layer), if desired. The sweatband can be useful to intercept perspiration prior to contact with the hands or eyes. VELCRO or other fastening device 182 can be used to facilitate adjustment or comfort.

The present invention may be better understood with reference to the following examples.

EXAMPLES

Unless otherwise indicated, the conventional superabsorbent material used in the Examples below was HYSORB 8850AD, available from BASF (having a place of business in Freeport, Tex., U.S.A.) and the fluff fiber used was COOSABSORB S, a bleached southern softwood Kraft pulp available from Bowater Inc., (having a place of business located in Greenville, S.C. U.S.A.).

Example 1

Figure 13:
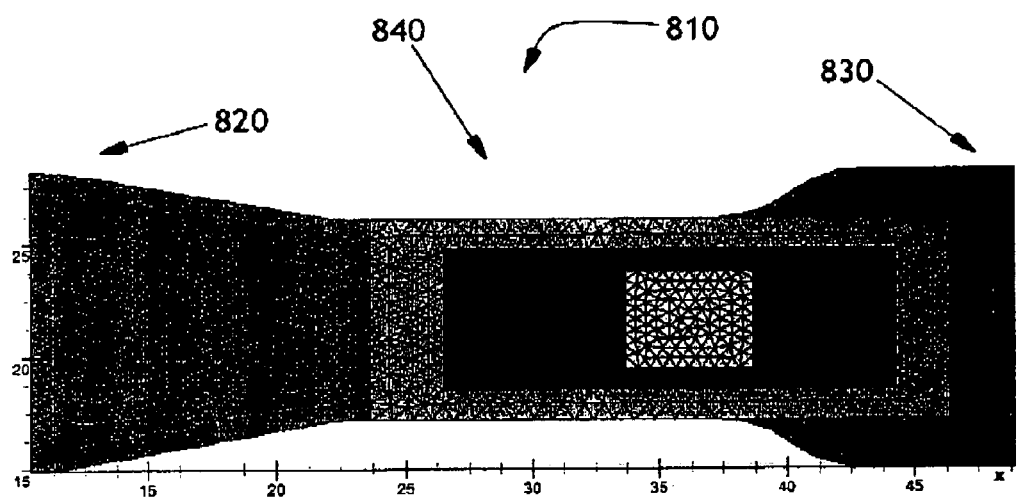
FIG. 13 is an absorbent system in the form of a pad in a laid flat condition.

A first series of computer simulations using finite element analysis was run to compare the fluid intake and fluid distribution of an absorbent system of the present invention with conventional absorbent systems. An exemplary absorbent system, in the form of a pad, can be seen in FIG. 13, shown generally as 810. A Comparative Example 1 was produced as a control, and had an absorbent system design that included "conventional" superabsorbent material. The conventional SAP had the following properties:
  Mean Particle Size=400 um;
  SAP Diffusion Coefficient=$2 \times 10^{-6}$ cm$^2$/sec; and
  SAP mCRC=30 g/g.

In comparison, Example 1, which represents absorbent systems comprising the superabsorbent polymer compositions of the present invention, had the following properties, which result in stepped capacity behavior:
  Mean Particle Size=400 um;
  SAP Diffusion Coefficient=$6 \times 10^{-6}$ cm$^2$/sec;
  For $1^{st}$ Insult and Hold Time: mCRC=8 g/g;
  For $2^{nd}$ Insult and Hold Time: mCRC=15 g/g;
  For $3^{rd}$ Insult and Hold Time: mCRC=21 g/g.

Additional input parameters of this first series of simulations were held constant for both absorbent systems, and include:

Three 70 ml fluid insults, followed by 4, 5, and 6 minute Hold times (i.e., the amount of time between or after each fluid insult), respectively.

Amount of superabsorbent material in the absorbent system=65 wt %

Density of the pad=0.24 g/cc

Surge material basis weight=76 gsm

Liquid Insult region=21.5 cm$^2$, located 11.4 cm from front edge 830 of pad 810 (FIG. 13)

Absorbent system was tested while in a prone position

Pad shape 840 (FIG. 13)

Results of this first series of computer simulations are presented in Table 1 below, which demonstrate the time to intake each of the three 70 ml insults.

TABLE 1

| System | 1$^{st}$ Intake Time (sec) | 2$^{nd}$ Intake Time (sec) | 3$^{rd}$ Intake Time (sec) |
|---|---|---|---|
| Comparative Example 1 | 50 | 85 | 131 |
| Example 1 | 58 | 90 | 101 |

The distribution behavior of the absorbent systems from this first series of simulations can also be characterized by the saturation level at the back 820 of the pad 810 at the end of each hold time period, as seen in Table 2 below and in FIG. 13:

TABLE 2

| System | 1$^{st}$ Hold Back Saturation (g/cm$^2$) | 2$^{nd}$ Hold Back Saturation (g/cm$^2$) | 3$^{rd}$ Hold Back Saturation (g/cm$^2$) |
|---|---|---|---|
| Comparative Example 1 | 0.0254 | 0.0808 | 0.165 |
| Example 1 | 0.0770 | 0.209 | 0.386 |

As can be seen from Table 1 and Table 2 above, the absorbent composite containing a stepped capacity superabsorbent shows generally similar intake properties as the conventional absorbent systems, but have substantially improved fluid distribution profiles.

Example 2

A second series of computer simulations using finite element analysis was run to determine the impact of changes in the characteristics of the stepped capacity behavior on the fluid intake and fluid distribution of absorbent systems. An exemplary absorbent system, in the form of a pad, can be seen in FIG. 13, shown generally as 810. Example 2 was an absorbent system design which included superabsorbent polymer composition of the present invention having stepped capacity behavior. Comparative Example 2 was an absorbent system design which included conventional superabsorbent material. The conventional superabsorbent material system had the following properties:

Mean Particle Size=400 um

SAP Diffusion Coefficient=2×10$^{-6}$ cm$^2$/sec

SAP mCRC=30 g/g

This simulation was a designed experiment which systematically varies the swelling rate and the 1$^{st}$, 2$^{nd}$, and 3$^{rd}$ step capacities of the superabsorbent. The eight conditions simulated as part of this designed experiment are list in Table 3 below:

TABLE 3

| Example | SAP Diffusion Coefficient (cm$^2$/sec) | SAP mCRC [1$^{st}$, 2$^{nd}$, 3$^{rd}$] (g/g) |
|---|---|---|
| 2-1 | 4 × 10$^{-6}$ | 6, 10, 20 |
| 2-2 | 4 × 10$^{-6}$ | 12, 20, 20 |
| 2-3 | 4 × 10$^{-6}$ | 12, 10, 30 |
| 2-4 | 4 × 10$^{-6}$ | 6, 20, 30 |
| 2-5 | 8 × 10$^{-6}$ | 12, 10, 20 |
| 2-6 | 8 × 10$^{-6}$ | 6, 20, 20 |
| 2-7 | 8 × 10$^{-6}$ | 6, 10, 30 |
| 2-8 | 8 × 10$^{-6}$ | 12, 20, 30 |

Additional input parameters of this second series of simulations were held constant for both absorbent systems, and include:

Three 70 ml fluid insults, followed by 4, 5, and 6 minute Hold times (i.e., the amount of time between or after each fluid insult), respectively Amount of superabsorbent material in the absorbent system=65 wt %

Density of the pad=0.24 g/cc

Surge material basis weight=76 gsm

Liquid insult region=21.5 cm$^2$, located 11.4 cm from front edge 830 of pad 810 (FIG. 13)

Absorbent system was tested while in a prone position

Pad Shape 840 (FIG. 13)

Results of this second series of computer simulations are presented in Table 4 below, which demonstrates the intake rate after each of the three 70 cc insults:

TABLE 4

| System | 1$^{st}$ Intake Rate (g/sec) | 2$^{nd}$ Intake Rate (g/sec) | 3$^{rd}$ Intake Rate (g/sec) |
|---|---|---|---|
| Comparative Example 2 | 1.4 | 0.82 | 0.53 |
| Example 2-1 | 0.69 | 0.16 | 0.40 |
| Example 2-2 | 1.33 | 0.88 | 0.27 |
| Example 2-3 | 1.33 | 0.10 | 0.71 |
| Example 2-4 | 0.69 | 0.93 | 0.87 |
| Example 2-5 | 1.73 | 0.11 | 0.58 |
| Example 2-6 | 0.89 | 1.43 | 0.37 |
| Example 2-7 | 0.89 | 0.23 | 1.15 |
| Example 2-8 | 1.73 | 1.17 | 1.06 |

Changes to the behavior of the stepped capacity superabsorbent also have an effect on fluid distribution. The distribution of fluid through the absorbent system can be characterized by the wet thickness in the target zone area at the end of each hold period. A lower wet thickness in the target zone area results as more fluid being distributed throughout the absorbent system. The wet thickness of the absorbent systems described above can be seen in Table 5 below.

TABLE 5

| System | 1$^{st}$ Hold Time Wet Thickness (cm) | 2$^{nd}$ Hold Time Wet Thickness (cm) | 3$^{rd}$ Hold Time Wet Thickness (cm) |
|---|---|---|---|
| Comparative Example 2 | 0.51 | 0.76 | 0.95 |
| Example 2-1 | 0.38 | 0.49 | 0.76 |
| Example 2-2 | 0.48 | 0.70 | 0.76 |
| Example 2-3 | 0.48 | 0.49 | 0.87 |
| Example 2-4 | 0.38 | 0.67 | 0.91 |
| Example 2-5 | 0.50 | 0.48 | 0.76 |
| Example 2-6 | 0.38 | 0.68 | 0.75 |
| Example 2-7 | 0.36 | 0.47 | 0.89 |

TABLE 5-continued

| System | 1st Hold Time Wet Thickness (cm) | 2nd Hold Time Wet Thickness (cm) | 3rd Hold Time Wet Thickness (cm) |
|---|---|---|---|
| Example 2-8 | 0.50 | 0.73 | 0.97 |

As can be seen, certain combinations of SAP capacity and diffusion coefficient at different stages can lead to maintaining liquid intake performance of commercial products, yet providing substantial distribution improvement (as seen by a decrease in wet thickness in the target location).

Further, the intake and thickness results illustrated in Tables 4 and 5 above, can be analyzed using known statistical methods to determine combinations of stepped capacity superabsorbent behavior that can lead to even more desirable intake and thickness results. This statistical analysis led to another simulation condition with the superabsorbent properties listed in Table 6 below. All other simulation parameters were held constant as described above.

TABLE 6

| System | SAP Diffusion Coefficient (cm²/sec) | SAP mCRC [1st, 2nd, 3rd] (g/g) |
|---|---|---|
| Example 2-9 | $7 \times 10^{-6}$ | 9, 16, 20 |

Results of the computer simulation using the properties from Table 6 are presented in Table 7 and Table 8 below, which demonstrates the intake rate for each of the three 70 ml insults, along with the wet thickness in the target area.

TABLE 7

| System | 1st Intake Rate (g/sec) | 2nd Intake Rate (g/sec) | 3rd Intake Rate (g/sec) |
|---|---|---|---|
| Example 2-9 | 1.36 | 0.88 | 0.66 |

It can be seen from Table 7 that composites of the present invention (i.e., comprising a stepped capacity superabsorbent polymer composition) result in longer wetted length and longer wetted area per gram of liquid loading. This demonstrates that the invention results in better liquid wicking/distribution when compared to absorbents having conventional SAP.

TABLE 8

| System | 1st Hold Wet Thickness (cm) | 2nd Hold Wet Thickness (cm) | 3rd Hold Wet Thickness (cm) |
|---|---|---|---|
| Example 2-9 | 0.45 | 0.65 | 0.83 |

As can be seen from Tables 7 and 8, the conditions simulated in Example 2-9 lead to Intake Rates similar to the comparative example, however the fluid distribution is improved which results in the wet thickness at the target zone to be substantially less than the control.

Example 3

In this example, stepped capacity behavior was demonstrated by controlling the salt concentration of an insult liquid used in each progressive insult. Three liquid insults (each totaling 70 ml with 15 minute intervals between each insult) were each added to an absorbent composite containing 60 wt % superabsorbent polymer composition of the present invention and the remainder fluff pulp (Example 3). For purposes of this example, the first insulting liquid was a solution of 8.0 wt % aqueous sodium chloride. The second and third insults were of a liquid solution of 0.9% aqueous sodium chloride. A comparative example (Comparative Example 3) was also tested as a control using 0.9% sodium chloride for all insults and represents an absorbent composite having conventional superabsorbent material. Each composite was placed in a horizontal position. The time for each liquid insult to enter the pad, the fluid distribution following a 15 minute hold time after each insult, and the thickness of the pad at the insult point after each hold time were measured. The results can be seen in Table 9 below.

TABLE 9

| Code | 1st Intake Rate (g/sec) | 2nd Intake Rate (g/sec) | 3rd Intake Rate (g/sec) | 1st Intake Thickness (mm) | 2nd Intake Thickness (mm) | 3rd Intake Thickness (mm) |
|---|---|---|---|---|---|---|
| Comparative Example 3 | 2.28 | 2.25 | 2.22 | 10.4 | 12.0 | 12.7 |
| Example 3 | 1.97 | 2.09 | 1.11 | 6.5 | 9.6 | 11.4 |

It can be seen from Table 9 that the intake rate for the absorbent composite of the present invention is generally similar to the intake rate of an absorbent composite having a conventional superabsorbent material. However, the thickness of the absorbent composite of the present invention is less than that of the comparative example. This indicates improved fluid distribution by the present invention, as well as greater comfort and fit for the user.

Figure 14:
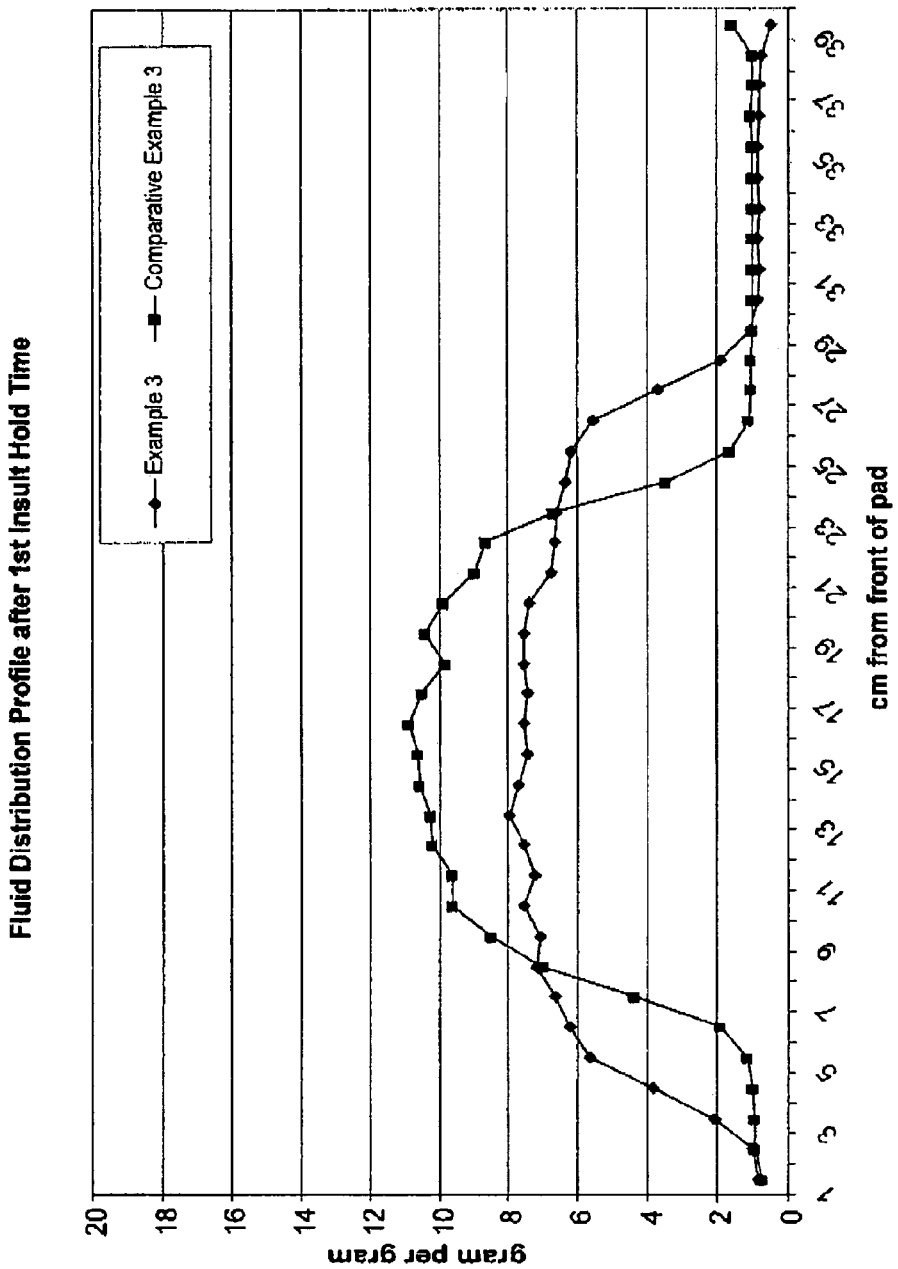
FIG. 14 is a graphical representation of fluid distribution after a first fluid insult and hold time.
Figure 15:
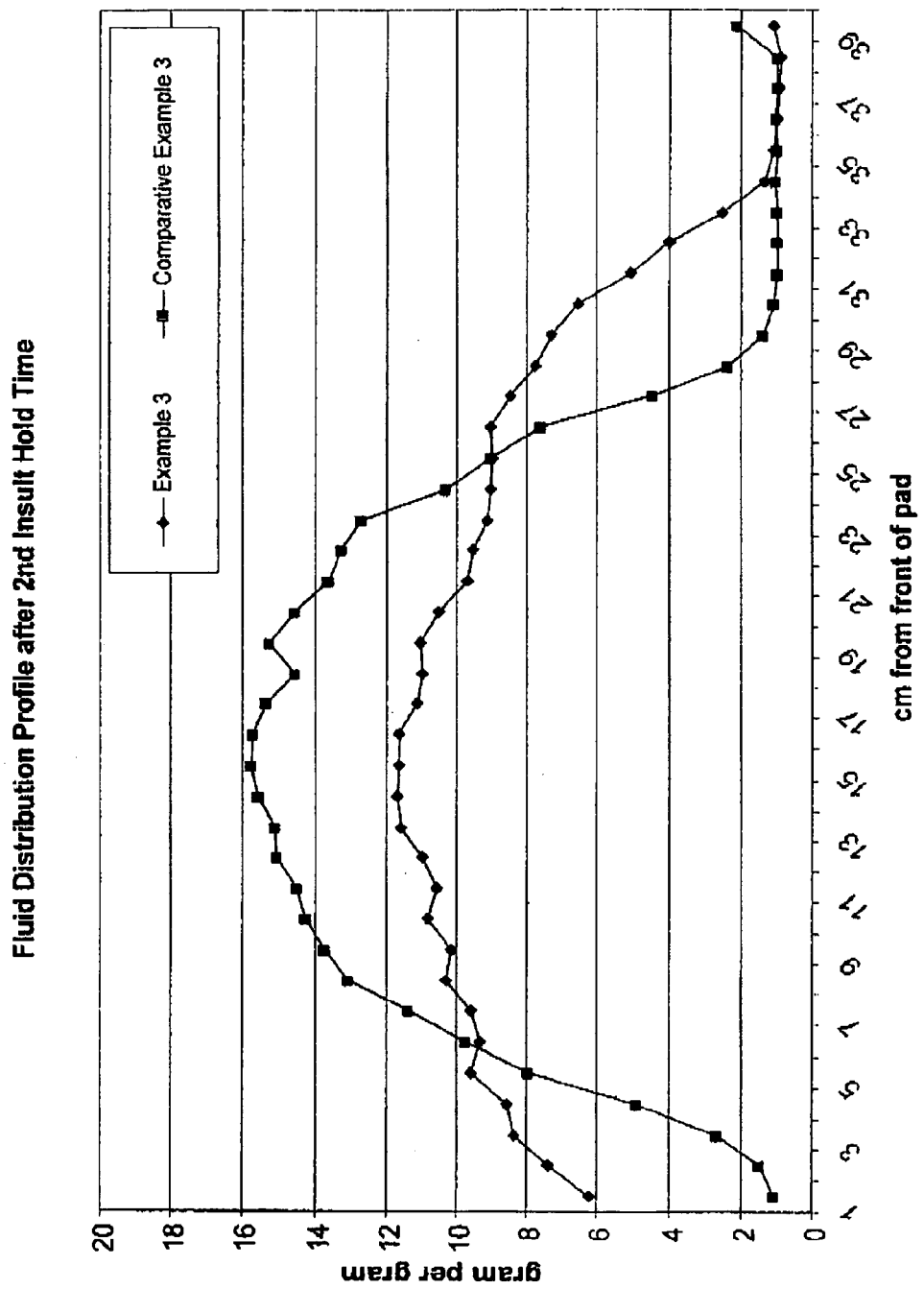
FIG. 15 is a graphical representation of fluid distribution after a second fluid insult and hold time.
Figure 16:
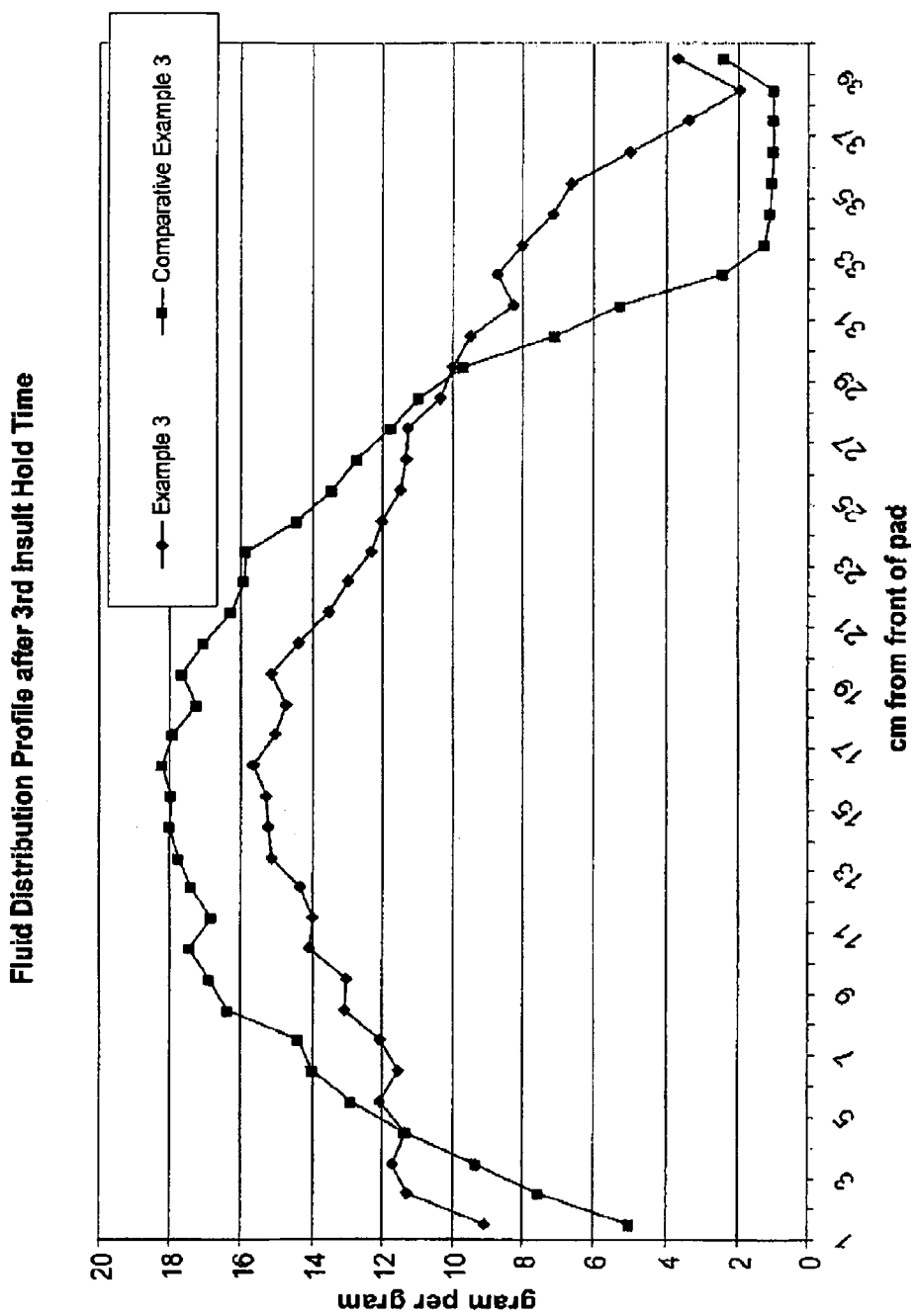
FIG. 16 is a graphical representation of fluid distribution after a $3^{rd}$ fluid insult and hold time.

In addition, FIGS. 14-16 show a graphical demonstration of the fluid distribution obtained in the examples after each insult, as measured using the Fluid Distribution Test described above. It can be seen that an absorbent composite of the present invention exhibits an improved fluid distribution when compared to an absorbent composite having conventional superabsorbent material.

Example 4

Static Mannequin testing, as described in the Mannequin Test Procedure above, was performed using absorbent articles in the form of a diaper. Each absorbent article of the present invention had a conventional hour glass shaped absorbent core which included 65% superabsorbent polymer composition having a stepped capacity behavior and 35% commercially available softwood fiber. Comparative (control) absorbent articles had a conventional hour glass shaped absorbent core which included 65% commercially available superabsorbent material and 35% commercially available softwood fiber. The absorbent core dry density was 0.24 g/cm³ and the absorbent articles each contained a 68 gsm intake layer (i.e., surge layer). Twenty-four diapers were used each for both control (i.e., comparative) codes, and for codes containing stepped capacity superabsorbent polymer compositions of the present invention. All codes were tested on appropriately-size mannequins.

For each code, twelve absorbent articles were tested in the sitting position and the remaining twelve articles were tested in the prone position. For each position, fluid was added to half of the products using "female" mannequins and fluid was added to the remaining six articles using "male" mannequins. Two insulting protocols were employed, such that 12 products for each code were insulted using a "70/70/70" insult protocol (i.e., three insults of 70 ml each) and the remaining 12 products for that code were insulted using a "35/70/70/70" protocol (i.e., four insults—one with 35 ml and then three with 70 ml each). The insult protocol is described in Table 10 below. The insult fluid (0.9 wt % aqueous sodium chloride solution) was kept at room temperature (about 20° C.).

It can be seen from Table 11 that absorbent articles of the present invention exhibit an improved fluid distribution when compared to articles comprising conventional superabsorbent materials.

Example 5

Intake testing, as described in the Fluid Intake Rate Test above, was performed on absorbent cores. Codes included comparative examples (controls) with insulting fluid at room

TABLE 10

Insult protocol for Example 4

70/70/70 Insult Scenario

|  | 1st Insult Part 1 | 1st Insult Part 2 | 2nd Insult Part 1 | 2nd Insult Part 2 | 3rd Insult Part 1 | 3rd Insult Part 2 | 4th Insult | 5th Insult | Subsequent Insults |
|---|---|---|---|---|---|---|---|---|---|
| Control | 45 ml of 0.9% NaCl | 25 ml of 0.9% NaCl | 45 ml of 0.9% NaCl | 25 ml of 0.9% NaCl | 45 ml of 0.9% NaCl | 25 ml of 0.9% NaCl | 70 ml of 6% NaCl | 70 ml of 6% NaCl | 70 ml of 0.9% NaCl |
| Stepped Capacity | 45 ml of 8% NaCl | 25 ml of 8% NaCl | 45 ml of 0.9% NaCl | 25 ml of 0.9% NaCl | 45 ml of 0.9% NaCl | 25 ml of 0.9% NaCl | 70 ml of 2.67% NaCl | 70 ml of 2.67% NaCl | 70 ml of 0.9% NaCl |

35/70/70/70 Insult Scenario

|  | 1st Insult | 2nd Insult Part 1 | 2nd Insult Part 2 | 3rd Insult Part 1 | 3rd Insult Part 2 | 4th Insult Part 1 | 4th Insult Part 2 | 5th Insult | 6th Insult | Subsequent Insults |
|---|---|---|---|---|---|---|---|---|---|---|
| Control | 35 ml of 0.9% NaCl | 45 ml of 0.9% NaCl | 25 ml of 0.9% NaCl | 45 ml of 0.9% NaCl | 25 ml of 0.9% NaCl | 45 ml of 0.9% NaCl | 25 ml of 0.9% NaCl | 70 ml of 6% NaCl | 70 ml of 6% NaCl | 70 ml of 0.9% NaCl |
| Stepped Capacity | 35 ml of 8% NaCl | 45 ml of 8% NaCl | 25 ml of 8% NaCl | 45 ml of 0.9% NaCl | 25 ml of 0.9% NaCl | 45 ml of 0.9% NaCl | 25 ml of 0.9% NaCl | 70 ml of 0.9% NaCl | 70 ml of 0.9% NaCl | 70 ml of 0.9% NaCl |

10 minute between insults
3 minutes between part 1 and 2 of insults

The absorbent articles were then insulted with the insult fluid as described above until each product leaked. The load at leak was noted for each product. The products were removed after the leak and were x-rayed, as described in Fluid Distribution Test described above to calculate the wetted length and wetted area of liquid in the product. The average of the ratio of wetted length to load at leak and wetted area to load at leak was calculated for each code. The results can be seen in Table 11 below.

TABLE 11

| Code | Average wetted length/load at leak (cm/ml) | Average wetted area/load at leak (cm$^2$/ml) |
|---|---|---|
| Comparative Example 4 (Control) | 0.115 | 1.098 |
| Example 4 (Stepped Capacity) | 0.156 | 1.483 | temperature (i.e., 0.9 wt % aqueous sodium chloride solution at about 20° C.); examples of the invention (Stepped Capacity) with the same insulting fluid also at room temperature; and examples of the invention (Stepped Capacity) with the same insulting fluid, but at a temperature of 50° C. All of the absorbent cores had a conventional hour glass shape similar to those in commercial products, a dry density of about 0.24 gm/cm$^3$, and were made with 65% superabsorbent material (either commercially available SAP or the superabsorbent polymer composition of the present invention) and 35% commercially available softwood fiber. The basis weight for each absorbent core was about 580 gsm. Each absorbent core was then insulted using the insulting sequence described in the Fluid Intake Rate Test described above. The specific liquids used for each portion of each insult series are indicated in Table 12 below.

TABLE 12

| Code | Temp (° C.) | 1$^{st}$ Insult Part 1 | 1$^{st}$ Insult Part 2 | 2$^{nd}$ Insult Part 1 | 2$^{nd}$ Insult Part 2 | 3$^{rd}$ Insult Part 1 | 3$^{rd}$ Insult Part 2 |
|---|---|---|---|---|---|---|---|
| Comparative Example 5 (Control) | 20 | 45 gm of 0.9% NaCl | 25 gm of 0.9% NaCl | 45 gm of 0.9% NaCl | 25 gm of 0.9% NaCl | 45 gm of 0.9% NaCl | 25 gm of 0.9% NaCl |
| Example 5-1 | 20 | 45 gm of 8% | 25 gm of 8% | 45 gm of | 25 gm of | 45 gm of | 25 gm of |

TABLE 12-continued

| Code | Temp (° C.) | 1st Insult Part 1 | 1st Insult Part 2 | 2nd Insult Part 1 | 2nd Insult Part 2 | 3rd Insult Part 1 | 3rd Insult Part 2 |
|---|---|---|---|---|---|---|---|
| (Stepped Capacity) | | NaCl | NaCl | 0.9% NaCl | 0.9% NaCl | 0.9% NaCl | 0.9% NaCl |
| Example 5-2 (Stepped Capacity) | 50 | 45 gm of 8% NaCl | 25 gm of 8% NaCl | 45 gm of 0.9% NaCl | 25 gm of 0.9% NaCl | 45 gm of 0.9% NaCl | 25 gm of 0.9% NaCl |

The intake rate, calculated based on the first part (45 gm) of each insult, can be seen in Table 13 below.

TABLE 13

| Code | Temp (° C.) | 1st Intake Rate (gm/sec) | 2nd Intake Rate (gm/sec) | 3rd Intake Rate (gm/sec) |
|---|---|---|---|---|
| Comparative Example 5 | 20 | 2.28 | 2.25 | 2.22 |
| Example 5-1 | 20 | 1.97 | 2.09 | 1.11 |
| Example 5-2 | 50 | 2.36 | 4.72 | 2.31 |

It can be seen from Table 13 that composites of the present invention exhibit a generally similar intake rate than those utilizing conventional SAP. Also, a higher temperature tends to improve the intake rate for composites of the present invention.

Example 6

Intake testing, as described in the Fluid Intake Rate Test above, was performed on absorbent cores. Codes included a Control (Comparative Example 6), representing composite that include conventional SAPs. Codes also included a Stepped Capacity original (Example 6-1), Stepped Capacity Lite (Example 6-2) and Stepped Capacity X-Lite (Example 6-3), each of which represented composites in accordance with the invention, as identified in Table 14 below. All of the absorbent cores had a conventional hour glass shape similar to those in commercial products, a dry density of about 0.24 gm/cm$^3$, and were made with 65% superabsorbent material (either commercially available SAP or superabsorbent polymer composition of the present invention) and 35% commercially available softwood fiber. The basis weight was about 580 gsm for all of the codes. Each absorbent core was then insulted using the insulting sequence described in the Fluid Intake Rate Test above. The specific liquids used for each portion of each insult series are indicated in Table 14 below.

TABLE 14

| Liquid Temp. (deg C.) | | 1st Insult Part 1 | 1st Insult Part 2 | 2nd Insult Part 1 | 2nd Insult Part 2 | 3rd Insult Part 1 | 3rd Insult Part 2 |
|---|---|---|---|---|---|---|---|
| Room | Control | 45 ml of 0.9% NaCl | 25 ml of 0.9% NaCl | 45 ml of 0.9% NaCl | 25 ml of 0.9% NaCl | 45 ml of 0.9% NaCl | 25 ml of 0.9% NaCl |
| 60 C. | Stepped Capacity original | 45 ml of 8% NaCl | 25 ml of 8% NaCl | 45 ml of 0.9% NaCl | 25 ml of 0.9% NaCl | 45 ml of 0.9% NaCl | 25 ml of 0.9% NaCl |
| 60 C. | Stepped Capacity Lite | 45 ml of 5% NaCl | 25 ml of 5% NaCl | 45 ml of 0.9% NaCl | 25 ml of 0.9% NaCl | 45 ml of 0.9% NaCl | 25 ml of 0.9% NaCl |
| 50 C. | Stepped Capacity X-Lite | 45 ml of 2.67% NaCl | 25 ml of 2.67% NaCl | 45 ml of 0.9% NaCl | 25 ml of 0.9% NaCl | 45 ml of 0.9% NaCl | 25 ml of 0.9% NaCl |

Intake Rate testing, as described in the Fluid Intake Rate Test procedure above, was performed on all codes of the absorbent cores (Control, Stepped Capacity original, Stepped Capacity Lite and Stepped Capacity X-Lite). The insulting protocol consisted of 3 insults of 70 ml, each split into two parts of 45 grams and 25 grams. The hold time between each insult group was 15 minutes (i.e., the time between the previous 45 g/25 g insult and the subsequent 45 g/25 g insult), and time between two parts of each insult was 2 minutes (i.e., the time between the 45 g insult and the 25 g insult).

The intake rate, calculated based on the first part (45 gm) of each insult, is listed in Table 15 below.

TABLE 15

| Code | 1st Intake Rate (gm/sec) | 2nd Intake Rate (gm/sec) | 3rd Intake Rate (gm/sec) |
|---|---|---|---|
| Comparative Example 6 (Control) | 2.04 | 2.40 | 1.92 |
| Example 6-1 (Stepped Capacity original) | 1.35 | 1.70 | 1.15 |
| Example 6-2 (Stepped Capacity Lite) | 1.64 | 2.77 | 1.86 |
| Example 6-3 (Stepped Capacity X-Lite) | 1.93 | 1.65 | 1.67 |

It can be seen from Table 15 that composites of the present invention exhibit a generally similar intake rate compared to those utilizing conventional SAP.

Example 7

Static Mannequin testing, as described in the Mannequin Test Procedure above was performed using absorbent articles in the form of a diaper. Each absorbent article of the present invention had a conventional hour glass shaped absorbent core which included 65% superabsorbent polymer composition having a stepped capacity behavior and 35% commercially available softwood fiber. Comparative (control) absorbent articles had a conventional hour glass shaped absorbent core which included 65% commercially available superabsorbent material and 35% commercially available softwood fiber. Each absorbent core dry density was 0.24 g/cm$^3$ and each absorbent article contained a 68 gsm intake layer (i.e., surge layer). Twelve articles were used for each of the following codes: Control (Comparative Example 7), Stepped Capacity original (Example 7-1), Stepped Capacity Lite (Example 7-2) and Stepped Capacity X-Lite (Example 7-3).

For each code, all of the articles were tested in the prone position with liquid added using "male" mannequins. Two insulting protocols were employed, such that 6 products for each code were insulted with "70/70/70" insult protocol (i.e., three insults of 70 ml each) and the remaining 6 products for that code were insulted with "35/70/70/70" protocol (i.e., four insults—one with 35 ml and then three with 70 ml each). The hold time between each insult group was 15 minutes (i.e., the time between the previous 45 g/25 g insult and the subsequent 45 g/25 g insult), and time between two parts of each insult was 2 minutes (i.e., the time between the 45 g insult and the 25 g insult).

The insult protocol is described in Table 16 below.

TABLE 16

| 70/70/70 Insult Scenaro | | | | | | | | |
|---|---|---|---|---|---|---|---|---|
| Liquid Temp. (deg C.) | | 1st Insult Part 1 | 1st Insult Part 2 | 2nd Insult Part 1 | 2nd Insult Part 2 | 3rd Insult Part 1 | 3rd Insult Part 2 | Subsequent Insults |
| Room | Control | 45 ml of 0.9% NaC | 25 ml of 0.9% NaCl | 45 ml of 0.9% NaCl | 25 ml of 0.9% NaCl | 45 ml of 0.9% NaCl | 25 ml of 0.9% NaCl | 70 ml of 0.9% NaCl |
| 60 C. | Stepped Capacity original | 45 ml of 8% NaCl | 25 ml of 8% NaCl | 45 ml of 0.9% NaCl | 25 ml of 0.9% NaCl | 45 ml of 0.9% NaCl | 25 ml of 0.9% NaCl | 70 ml of 0.9% NaCl |
| 60 C. | Stepped Capacity Lite | 45 ml of 5% NaCl | 25 ml of 5% NaCl | 45 ml of 0.9% NaCl | 25 ml of 0.9% NaCl | 45 ml of 0.9% NaCl | 25 ml of 0.9% NaCl | 70 ml of 0.9% NaCl |
| 50 C. | Stepped Capacity X-Lite | 45 ml of 2.67% NaCl | 25 ml of 2.67% NaCl | 45 ml of 0.9% NaCl | 25 ml of 0.9% NaCl | 45 ml of 0.9% NaCl | 25 ml of 0.9% NaCl | 70 ml of 0.9% NaCl |

| 35/70/70/70 Insult Scenario | | | | | | | | |
|---|---|---|---|---|---|---|---|---|
| Liquid Temp. (deg C.) | | 1st Insult | 2nd Insult Part 1 | 2nd Insult Part 2 | 3rd Insult Part 1 | 3rd Insult Part 2 | 4th Insult Part 1 | 4th Insult Part 2 | Subsequent Insults |
| Room | Control | 35 ml of 0.9% NaCl | 45 ml of 0.9% NaCl | 25 ml of 0.9% NaCl | 45 m of 0.9% NaCl | 25 ml of 0.9% NaCl | 45 ml of 0.9% NaCl | 25 ml of 0.9% NaCl | 70 ml of 0.9% NaCl |
| 60 C. | Stepped Capacity original | 35 ml of 8% NaCl | 45 ml of 8% NaCl | 25 ml of 8% NaCl | 45 m of 0.9% NaCl | 25 ml of 0.9% NaCl | 45 ml of 0.9% NaCl | 25 ml of 0.9% NaCl | 70 ml of 0.9% NaCl |
| 60 C. | Stepped Capacity Lite | 35 ml of 5% NaCl | 45 ml of 5% NaCl | 25 ml of 5% NaCl | 45 m of 0.9% NaCl | 25 ml of 0.9% NaCl | 45 ml of 0.9% NaCl | 25 ml of 0.9% NaCl | 70 ml of 0.9% NaCl |
| 50 C. | Stepped Capacity X-Lite | 35 ml of 2.57% NaCl | 45 ml of 2.57% NaCl | 25 ml of 2.57% NaCl | 45 m of 0.9% NaCl | 25 ml of 0.9% NaCl | 45 ml of 0.9% NaCl | 25 ml of 0.9% NaCl | 70 ml of 0.9% NaCl |

The insult fluid (0.9 wt % aqueous sodium chloride solution) was set at room temperature (~20° C.) for the Control; at 60° C. for both Stepped Capacity original and Stepped Capacity Lite, and 50° C. for Stepped Capacity X-Lite. The absorbent articles were then insulted with the insult fluids as described above until each product leaked. The load at leak was noted for each product. The products were removed after the leak and were x-rayed, as described in Fluid Distribution Test described above to calculate the wetted area of liquid in each product. The average of the ratio of wetted area to load at leak was calculated for each code, and is listed in Table 17 below.

TABLE 17

| Code | Average wetted area/load at leak (cm²/ml) |
|---|---|
| Comparative Example 7 (Control) | 1.07 |
| Example 7-1 (Stepped Capacity original) | 1.46 |
| Example 7-2 (Stepped Capacity Lite) | 1.40 |

TABLE 17-continued

| Code | Average wetted area/load at leak (cm²/ml) |
|---|---|
| Example 7-3 (Stepped Capacity X-Lite) | 1.20 |

It can be seen from Table 17 that the composites of the present invention (Stepped Capacity original, Stepped Capacity Lite, and Stepped Capacity X-Lite) result in longer wetted length per gm of liquid loading compared to a composite having conventional SAP. This demonstrates that invention results in better liquid wicking/distribution.

Example 8

The Swelling Rate of superabsorbent materials, such as those used in the Examples above, were measured as described in the Swelling Rate Test described above. Various salt concentrations and temperatures were used to measure the influence of these two characteristics on the Swelling Rate. The results of the testing are summarized in Table 18 below.

TABLE 18

| Temperature (° C.) | NaCl concentration of test fluid (%) | Swelling Rate (cm²/sec) |
|---|---|---|
| 22 | 0.9 | 1.66 |
| 50 | 0.9 | 3.39 |
| 60 | 2.0 | 3.14 |
| 60 | 3.3 | 2.50 |
| 60 | 5.0 | 2.00 |

It can be seen from Table 18 that Swelling Rate increases with increasing temperature, and decreases with increasing salt (NaCl) concentration.

It will be appreciated that details of the foregoing examples, given for purposes of illustration, are not to be construed as limiting the scope of this invention. Although only a few exemplary embodiments of this invention have been described in detail above, those skilled in the art will readily appreciate that many modifications are possible in the examples without materially departing from the novel teachings and advantages of this invention. For example, features described in relation to one example may be incorporated into any other example of the invention.

Accordingly, all such modifications are intended to be included within the scope of this invention, which is defined in the following claims and all equivalents thereto. Further, it is recognized that many embodiments may be conceived that do not achieve all of the advantages of some embodiments, particularly of the desirable embodiments, yet the absence of a particular advantage shall not be construed to necessarily mean that such an embodiment is outside the scope of the present invention. As various changes could be made in the above constructions without departing from the scope of the invention, it is intended that all matter contained in the above description shall be interpreted as illustrative and not in a limiting sense.

What is claimed is:

1. An absorbent composition comprising:
   a superabsorbent polymer composition having an initial absorbent capacity of at least about 5 grams saline per gram of superabsorbent polymer composition; and
   a first triggering mechanism having a first release time of between about 5 and 60 minutes;
   wherein the superabsorbent polymer composition has a second absorbent capacity of at least about 25% greater than the first absorbent capacity as measured by the mCRC Test;
   a second triggering mechanism having a second release time of between about 10 and 120 minutes and at least about 5 minutes longer than the first release time;
   wherein the superabsorbent polymer composition has a third absorbent capacity of at least about 25% greater than the second absorbent capacity as measured by the mCRC Test.

2. The absorbent composition of claim 1 further comprising:
   a third triggering mechanism having a third release time of between about 15 and 180 minutes and at least about 5 minutes longer than the second release time;
   wherein the superabsorbent polymer composition has a fourth absorbent capacity of at least about 25% greater than the third absorbent capacity as measured by the mCRC Test.

3. The absorbent composition of claim 2 further comprising:
   a fourth triggering mechanism having a fourth release time of between about 20 and 240 minutes and at least about 5 minutes longer than the third release time;
   wherein the superabsorbent polymer composition has a fifth absorbent capacity of at least about 25% greater than the fourth absorbent capacity as measured by the mCRC Test.

4. The absorbent composition of claim 1 wherein the swelling rate of the superabsorbent polymer composition has a swelling rate that is at least about 20% greater than the swelling rate of a conventional superabsorbent material as measured by the Swelling Rate Test.

5. The absorbent composition of claim 4 wherein the swelling rate of the superabsorbent polymer composition has a swelling rate that is at least about 50% greater than the swelling rate of a conventional superabsorbent material as measured by the Swelling Rate Test.

6. The absorbent composition of claim 5 wherein the swelling rate of the superabsorbent polymer composition has a swelling rate that is at least about 100% greater than the swelling rate of a conventional superabsorbent material as measured by the Swelling Rate Test.

7. An absorbent composite comprising:
   a water-insoluble fibrous matrix;
   a superabsorbent polymer composition having an initial absorbent capacity of at least about 5 grams saline per gram of superabsorbent polymer composition; and
   a first triggering mechanism having a first release time of between about 5 and 60 minutes;
   wherein the superabsorbent polymer composition has a second absorbent capacity of at least about 25% greater than the first absorbent capacity as measured by the mCRC Test;
   a second triggering mechanism having a second release time of between about 10 and 120 minutes and at least about 5 minutes longer than the first release time;
   wherein the superabsorbent polymer composition has a third absorbent capacity of at least about 25% greater than the second absorbent capacity as measured by the mCRC Test.

8. The absorbent composite of claim 7 wherein the superabsorbent polymer composition further comprises:
   a third triggering mechanism having a third release time of between about 15 and 180 minutes and at least about 5 minutes longer than the second release time;
   wherein the superabsorbent polymer composition has a fourth absorbent capacity of at least about 25% greater than the third absorbent capacity as measured by the mCRC Test.

9. The absorbent composite of claim 8 wherein the superabsorbent polymer composition further comprises:
   a fourth triggering mechanism having a fourth release time of between about 20 and 240 minutes and at least about 5 minutes longer than the third release time;
   wherein the superabsorbent polymer composition has a fifth absorbent capacity of at least about 25% greater than the fourth absorbent capacity as measured by the mCRC Test.

10. The absorbent composite of claim 8 wherein the swelling rate of the superabsorbent polymer composition has a swelling rate that is at least about 20% greater than the swelling rate of a conventional superabsorbent material as measured by the Swelling Rate Test.

11. The absorbent composite of claim 10 wherein the swelling rate of the superabsorbent polymer composition has a swelling rate that is at least about 50% greater than the swelling rate of a conventional superabsorbent material as measured by the. Swelling Rate Test.

12. The absorbent composite of claim 11 wherein the swelling rate of the superabsorbent polymer composition has a swelling rate that is at feast about 100% greater than the swelling rate of a conventional superabsorbent material as measured by the Swelling Rate Test.

* * * * *